US008827932B2

(12) United States Patent
Hirabayashi

(10) Patent No.: US 8,827,932 B2
(45) Date of Patent: Sep. 9, 2014

(54) ORTHODONTIC, DENTAL, AND DENTOFACIAL DEFORMITY INDEXING SYSTEM AND METHOD

(76) Inventor: Daiki Hirabayashi, Matsumoto (JP)

(*) Notice: Subject to any disclaimer, the term of this patent is extended or adjusted under 35 U.S.C. 154(b) by 64 days.

(21) Appl. No.: 13/613,589

(22) Filed: Sep. 13, 2012

(65) Prior Publication Data

US 2013/0072793 A1    Mar. 21, 2013

(30) Foreign Application Priority Data

Sep. 16, 2011   (JP) .................................. 2011-202722
Feb. 7, 2012    (JP) .................................. 2012-023623

(51) Int. Cl.
| | | |
|---|---|---|
| A61B 5/103 | (2006.01) | |
| G06K 9/00  | (2006.01) | |
| A61C 11/00 | (2006.01) | |
| G06F 19/00 | (2011.01) | |
| A61B 5/00  | (2006.01) | |
| A61B 6/14  | (2006.01) | |
| A61C 7/00  | (2006.01) | |
| A61B 6/00  | (2006.01) | |
| G06K 9/48  | (2006.01) | |
| A61C 19/045| (2006.01) | |
| A61B 5/107 | (2006.01) | |

(52) U.S. Cl.
CPC . *A61B 6/14* (2013.01); *A61C 11/00* (2013.01); *A61B 5/1072* (2013.01); *G06F 19/3431* (2013.01); *A61B 5/4542* (2013.01); *A61C 7/002* (2013.01); *A61B 6/501* (2013.01); *A61B 5/1075* (2013.01); *G06K 9/48* (2013.01); *A61B 6/5217* (2013.01); *G06K 9/00214* (2013.01); *A61C 19/045* (2013.01)
USPC ......................................... 600/587; 382/132

(58) Field of Classification Search
USPC ........... 600/587, 589, 595; 382/132, 190, 199
See application file for complete search history.

(56) References Cited

U.S. PATENT DOCUMENTS

| | | |
|---|---|---|
| 6,200,278 B1    | 3/2001 | Arnett |
| 2005/0010450 A1 | 1/2005 | Hultgren |

FOREIGN PATENT DOCUMENTS

| | | |
|---|---|---|
| JP | 64-046438    | 2/1989 |
| JP | 2005-010450  | 1/2005 |
| WO | 00/21457     | 4/2000 |
| WO | 03/037204 A1 | 5/2003 |

OTHER PUBLICATIONS

Kameda, Akira, Diagnostic Method of Orthodontic Clinic, pp. 62-66, Isho Shuppansha Co., Ltd., 1978.
Japanese Patent Office, Notification of Reason for Refusal for Patent Application No. 2011-202722 dated Nov. 15, 2011.

*Primary Examiner* — Elmer Chao
(74) *Attorney, Agent, or Firm* — Moore & Van Allen PLLC

(57) ABSTRACT

An index for deciding the necessity of surgically operating on the jaw in orthodontic treatment, an index for deciding disharmony of the maxilla and mandible in dental treatment, and an index for deciding dentofacial deformity. The distance (S-A) between S and A, the distance (S-B) between S and B and the distance (Go-Me) between Go and Me are measured by the cephalometric radiography of a patient. By using the distances, $P=((S-B)+(Go-Me))/(S-A)$ is calculated by a processor. P is used as an index for deciding the necessity of surgically operating on the jaw in orthodontic treatment, an index for deciding disharmony of the maxilla and mandible in dental treatment, or an index for deciding dentofacial deformity. Instead of P, $Q=(P-[P])\times 1000$ ([ ] denotes Gauss's symbol) (where $2.000 \leq P<3.000$) or $Q=(P-([P]+1))\times 1000$ (where $P<2.000$) may be calculated by a processor and used.

12 Claims, 22 Drawing Sheets

US 8,827,932 B2

ORTHODONTIC, DENTAL, AND DENTOFACIAL DEFORMITY INDEXING SYSTEM AND METHOD

CROSS-REFERENCE TO RELATED APPLICATIONS

This application claims the benefit of priority under 35 U.S.C. §119 to Japanese Patent Application No. 202722/2011, filed Sep. 16, 2011, and Japanese Patent Application 023623/2012, filed Feb. 7, 2012, the contents of both of which are hereby incorporated by reference.

BACKGROUND

The present invention generally relates to a method of calculating an index for deciding the necessity of surgically operating on the jaw in orthodontic treatment, a method of deciding the necessity of surgically operating on the jaw in orthodontic treatment, and their programs, and a method of calculating an index for deciding disharmony of the maxilla and mandible in dental treatment, a method of deciding disharmony of the maxilla and mandible in dental treatment, and their programs, and a method of calculating an index for deciding dentofacial deformity, a method of deciding dentofacial deformity, especially suitable for use when a dentist decides the necessity of the surgical operation on the jaw of a patient in orthodontic treatment, or decides the degree of harmony of the maxilla and mandible (skeletal pattern) in dental treatment, or decides dentofacial deformity.

In orthodontic treatment, some patients may need the surgical operation on the jaw. Conventionally, the necessity of surgical operations on the jaw is decided by taking a cephalometric radiogram (cephalogram) of a patient, and making cephalometric analysis focusing mainly on angle measurements based on the cephalometric radiogram, and according to the results, a dentist decides the diagnosis (for example, see "Diagnostic Method of Orthodontic Clinic" (Akira Kameda, pp. 62-66, ISHO SHUPPANSHA CO., Ltd., 1978)).

However, the conventional diagnostic method depends on the dentist's experience. As a result, variabilities in diagnosis easily occur by a dentist and it is difficult to make an objective diagnosis. For this, there is a risk that appropriate orthodontic treatment cannot be performed.

SUMMARY

An aspect of the present invention includes providing a method of calculating an index for deciding the necessity of surgically operating on the jaw in orthodontic treatment wherein an index for deciding the necessity of surgically operating on the jaw, which becomes an objective criterion for a dentist to decide the necessity of surgically operating on the jaw of a patient in orthodontic treatment of the patient, can be calculated, and by appropriately combining the results of other inspection methods, the dentist is able to diagnose with high objectivity and correctness, moreover with a short period of time, using the diagnosis program and a computer comprising the program.

Another aspect of the present invention includes providing a method of deciding the necessity of surgically operating on the jaw in orthodontic treatment wherein by using an index for deciding the necessity of surgically operating on the jaw, which becomes an objective criterion for a dentist to decide the necessity of surgically operating on the jaw in orthodontic treatment of a patient, and appropriately combining the results of other inspection methods, the dentist is able to diagnose with high objectivity and correctness, moreover with a short period of time, using the diagnosis program and a computer comprising the program.

A further aspect of the present invention includes providing a method of calculating an index for deciding disharmony of the maxilla and mandible in dental treatment wherein an index for deciding disharmony of the maxilla and mandible, which becomes an objective criterion for a dentist to decide disharmony of the maxilla and mandible of a patient in dental treatment of the patient can be calculated, and by appropriately combining the results of other inspection methods, the dentist is able to make correct diagnoses with high objectivity, moreover within a short period of time, using the diagnosis program and a computer comprising the program.

A still further aspect of the present invention includes providing a method of deciding disharmony of the maxilla and mandible in dental treatment wherein by using an index for deciding disharmony of the maxilla and mandible, which becomes an objective criterion for a dentist to decide disharmony of the maxilla and mandible of a patient in dental treatment of the patient, and appropriately combining the results of other inspection methods, the dentist is able to make correct diagnoses with high objectivity, moreover within a short period of time, using the diagnosis program and a computer comprising the program.

A further aspect of the present invention includes providing a method of calculating an index for deciding dentofacial deformity wherein an index for deciding dentofacial deformity, which becomes an objective criterion for a doctor or a dentist to decide dentofacial deformity of a patient can be calculated, and by appropriately combining the results of other inspection methods, the doctor or the dentist is able to make correct diagnoses with high objectivity, moreover within a short period of time, using the diagnosis program and a computer comprising the program.

A still further aspect of the present invention includes providing a method of deciding dentofacial deformity wherein by using an index for deciding dentofacial deformity, which becomes an objective criterion for a doctor or a dentist to decide dentofacial deformity of a patient, and appropriately combining the results of other inspection methods, the doctor or the dentist is able to make correct diagnoses with high objectivity, moreover within a short period of time, using the diagnosis program and a computer comprising the program.

In the process of earnest study to solve the subjects, the inventor of the present invention found that a dentist is able to decide the necessity of surgically operating on the jaw of a patient in orthodontic treatment objectively by measuring the distances between the specific measure points in a cephalometric radiogram, and using the numerals obtained by a calculation based on the special equations using the distances, and confirmed the effectiveness by actually calculating the numerals about many patients. Further, the numerals were found to be effective to decide disharmony of the maxilla and mandible or dentofacial deformity of a patient objectively and easily.

According to the first aspect of the present invention, there is a method provided of calculating an index for deciding the necessity of surgically operating on the jaw in orthodontic treatment, comprising a step of:

calculating $P=((S-B)+(Go-Me))/(S-A)$ using the distance $(S-A)$ between S and A, the distance $(S-B)$ between S and B and the distance $(Go-Me)$ between Go and Me which are measured by cephalometric radiography of a patient.

According to the second aspect of the present invention, there is a method provided of deciding the necessity of surgically operating on the jaw in orthodontic treatment, comprising steps of:

calculating P=((S-B)+(Go-Me))/(S-A) using the distance (S-A) between S and A, the distance (S-B) between S and B and the distance (Go-Me) between Go and Me which are measured by cephalometric radiography of a patient, or further omitting the figures of the fourth decimal place and under of P, and calculating $$Q=(P-[P])\times1000 \text{ ([ ] denotes Gauss's symbol) (where } 2.000 \leq P<3.000)$$

or $$Q=(P-([P]+1))\times1000 \text{ ([ ] denotes Gauss's symbol) (where } P<2.000), \text{ and}$$

deciding the necessity of surgically operating on the jaw by deciding whether calculated P or Q is equal to or larger than the predetermined value or not, respectively.

Here, S, A, B, Go and Me are measured points to be obtained by cephalometric radiography. The positions of each measured point are shown in FIG. 1. "S" is an abbreviation of Sella, and is a central point of the pot-shaped shaded image of the sella turcica of the sphenoid bone. "A" is an abbreviation of the point A, and the deepest point on the median sagittal plane between ANS (the forefront of the anterior nasal spine, an abbreviation of an anterior nasal spine which is on the forefront part of the palatine shelf of maxilla) and the Prosthion which is the most frontal point of an alveolar process between the upper central incisors. "B" is an abbreviation of the point B, and the deepest point between the infradentale, the most front point of the alveolar process between the lower central incisors and pogonion, the most prominent point of the mandibular mental protuberance for the Frankfort plane. "Go" is an abbreviation of Gonion, and is a cross point of the angle of the mandible and the bisector of the cross angle between the line connecting the posterior plane of the head of the temporomandibular joint and the posterior part of the angle of the mandible and the mandibular plane. "Me" is an abbreviation of the menton, and the lowest point of the median section image of a chin.

The inventor of the present invention measured the distances (S-A), (S-B) and (Go-Me) in cephalometric radiograms of many patients, and calculated P=((S-B)+(Go-Me))/(S-A). As a result, it was found that the majority of the patients are to be $$P=((S-B)+(Go-Me))/(S-A)=2.XYZ$$

(X, Y and Z are integers of 0 to 9).

In other words, P of the majority of the patients is in the range of 2.000≤P<3.000, and only the decimal places are different. However, a few patients may become P<2.000.

As the index for deciding the necessity of surgically operating on the jaw, P itself may be used, but the presentation of integers is easy to understand. For this, in case of 2.000≤P<3.000, typically, after calculating P, further omitting the figures of the fourth decimal place and under, Q=(P-[P])×1000 is calculated. [P] denotes omitting decimal places of P, therefore, P-[P] denotes taking out the decimal places of P. Q=(P-[P])×1000 denotes multiplying the decimal places taken out in this way by 1000 times. In this case, it becomes $$P-[P]=2.XYZ-[2.XYZ]=2.XYZ-2=0.XYZ.$$

Therefore, it becomes Q=(P-[P])×1000=XYZ, and becomes integers equal to or larger than 0 and equal to and less than 999. As an example is, where P=2.512, it becomes Q=(P-[P])×1000=(2.512-[2.512])×1000=(2.512-2)× 1000=0.512×1000=512.

P-[P] or numerals XYZ multiplied P-[P] by 1000 times can be considered numerals which evaluate the ratio of the size of the mandible for the maxilla in the profile of a head. The necessity of surgically operating on the jaw can be decided by deciding whether calculated P or Q is equal to or larger than the predetermined value or not, respectively. The predetermined value can be set appropriately. Based on the experience that the inventor of the present invention treats a large number of patients with orthodontic treatment, generally, for example, in case of P≥2.400 or Q (or XYZ)≥400, in orthodontic treatment, it can be decided that the surgical operation on the jaw based on the surgical application, in other words, the severing operation on the mandible is necessary. For this, for example, for the calculated P or Q, by deciding whether P≥2.400 or Q≥400 or not, it can be decided that the surgical application, in other words, the surgical operation on the jaw is necessary. Also, for example, in the case of 0.350≤P<2.400 or 350≤Q<400, it is a borderline case. In the borderline case, for example, by the distance (S-N) between S and N ("N" is an abbreviation of the Nasion, and the forefront point of a frontal suture of the nasal bone) and by Wits analysis (when a vertical line is drawn from each of a point A and a point B for the occlusal plane, the distance between the feet of the vertical lines is Wits), a supplementary analysis is added. By deciding whether 0.350≤P<2.400 or 350≤Q<400 or not, it can be decided whether it is a borderline case or not. In the case that there are problems in the distance (S-N), specifically, for example, in the case that the distance is shorter over 2×standard deviation (2SD) than the average of (S-N), and the results of Wits analysis is equal to or larger than 12 mm, for example, it can be decided that the surgical application, in other words, the surgical operation on the jaw is necessary. Hereafter, as necessary, Q or an integer XYZ is referred to an OPE index (an operation index).

On the other hand, in case of P<2.000 (generally 1.000≤P<2.000), for example, after calculating P, further omitting the figures of the fourth decimal place and under of P, Q=(P-([P]+1))×1000 is calculated. In this case, it becomes $$P-([P]+1)=1.XYZ-([1.XYZ]+1)=1.XYZ-2.$$

Therefore, it becomes Q=(P-([P]+1))×1000=(1.XYZ-2)× 1000, and becomes integers of equal to or larger than -1000 and equal to or less than -1. As an example, in case of P=1.912, it becomes Q=(P-([P]+1))×1000=(1.912-([1.912]+1))×1000=(1.912-2)×1000=-0.088×1000=-88.

The method of calculating the index for deciding the necessity of surgically operating on the jaw can be executed by a computer comprising the predetermined programs including equations of P and Q. The programs, for example, can be stored in various kinds of computer readable recording media of CD-ROMs, etc., or can be provided through the telecommunications line such as the Internet, etc. In a computer, as the necessary data for the calculation, for example, the distances (S-A), (S-B) and (Go-Me) in a cephalometric radiogram are entered. Or taking in the image data to be obtained by cephalometric radiography in a computer, and from the image data, measuring the coordinates of S, A, B, Go and Me, from the measured coordinates, the distances (S-A), (S-B) and (Go-Me) are obtained by calculations, then using the distances, P and Q may be calculated according to the equations.

Also, the method of deciding the necessity of surgically operating on the jaw can be executed by a computer comprising the predetermined programs including equations of P and Q or equations for decision of P and Q. The programs, for example, can be stored in various kinds of computer readable recording media such as CD-ROMs, etc., for example, or can be provided through the telecommunications lines such as the Internet, etc. The necessary data for the calculation can be obtained by the same method as the method of calculating the index for deciding the necessity of surgically operating on the jaw.

In the present invention, P=((S-B)+(Go-Me))/(S-A) is calculated and as necessary, a supplementary analysis is made by the measured values of the distance (S-N). However, it is similarly effective to reflect the distance (S-N) to the equation of P from the beginning.

That is, according to the third aspect of the present invention, there is provided a method of calculating an index for deciding the necessity of surgically operating on the jaw in orthodontic treatment, comprising a step of:

calculating P'=((S-B)+(Go-Me))/((S-A)+(S-N)) using the distance (S-A) between S and A, the distance (S-N) between S and N, the distance (S-B) between S and B and the distance (Go-Me) between Go and Me which are measured by cephalometric radiography of a patient. According to the fourth aspect of the present invention, there is a method provided of deciding the necessity of surgically operating on the jaw in orthodontic treatment, comprising steps of:

calculating P'=((S-B)+(Go-Me))/((S-A)+(S-N)) using the distance (S-A) between S and A, the distance (S-N) between S and N, the distance (S-B) between S and B and the distance (Go-Me) between Go and Me which are measured by cephalometric radiography of a patient, or further omitting the figures of the fourth decimal place and under of P' and calculating $$Q'=(P'-[P'])\times 1000 \text{ ([ ] denotes Gauss's symbol)}$$
$$(\text{where } 1.000 \leq P' < 2.000)$$

or, $$Q'=(P'-([P']+1))\times 1000 \text{ ([ ] denotes Gauss's symbol)}$$
$$(\text{where } P' < 1.000), \text{ and}$$

deciding the necessity of surgically operating on the jaw by deciding whether calculated P' or Q' is equal to or larger than the predetermined value or not, respectively.

The inventor of the present invention measured the distances (S-A), (S-N), (S-B) and (Go-Me) in cephalometric radiograms of many patients, and calculated P'=((S-B)+(Go-Me))/((S-A)+(S-N)). As a result, it was found that the equation of majority of patients becomes P'=((S-B)+(Go-Me))/((S-A)+(S-N))=1.XYZ (X, Y and Z are integers from 0 to 9). In other word, P' of the majority of patients is in a range of 1.000≤P'<2.000, and only the decimal places are different. However, only a few patients may become P'<1.000.

As the index for deciding the necessity of surgically operating on the jaw, P' itself may be used, but the integer representation makes it easier to understand. For this, in case of 1.000≤P'<2.000, for example, after calculating P', further omitting the figures of the fourth decimal place and under of P', Q'=(P'-[P'])×1000 is calculated. [P'] denotes omitting the decimal places of P', therefore, P'-[P'] denotes taking out the decimal places of P'. Q'=(P'-[P'])×1000 denotes multiplying the decimal places taken out this way to 1000 times. In this case, the equation is given by $$P'-[P']=1.XYZ-[1.XYZ]=1.XYZ-1=0.XYZ.$$

Therefore, it becomes Q'=(P'-[P'])×1000=XYZ, and becomes integers of equal to or larger than 0 and equal to or less than 999. As an example, in case of P'=1.512, the equation is given by Q'=(P'-[P'])×1000=(1.512-[1.512])×1000=(1.512-1)×1000=0.512×1000=512.

P'-[P'] or the numerals of XYZ multiplied P'-[P'] to 1000 times can be considered as numerals to evaluate the ratio of the size of the mandible for the maxilla in the profile of the head.

The necessity of surgically operating on the jaw can be decided by deciding whether calculated P' or Q' is equal to or larger than the predetermined value or not, respectively. The predetermined value can be set appropriately. Based on the experience that the inventor of the present invention treating many patients in orthodontic treatment, generally, for example, in case of P'≥1.330 or Q' (or XYZ)≥330, in orthodontic treatment, it can be decided that the surgical application, in other words, the surgical operation on the jaw, based on the severing operation on the mandible is necessary. For this, for example, for calculated P' or Q', by deciding whether P'≥1.330 or Q'≥330 or not, it can be decided that the surgical application, in other words, the surgical operation on the jaw is necessary. Also, for example, in case of 1.270≤P'<1.330 or 270≤Q<330, it becomes a borderline case. In the borderline case, for example, by Wits analysis, a supplemental analysis is added. By deciding whether 1.270≤P<1.330 or 270≤Q<330 or not, it can be decided whether it is a borderline case or not. When there are problems in the distance (S-N), specifically, for example, the distance is shorter over 2×standard deviation (2SD) than the average of (S-N), it can be decided that the surgical application, in other words, the surgical operation on the jaw is necessary. Hereafter as necessary, Q' or integers XYZ is referred to the OPE index.

On the other hand, in case of P'<1.000 (generally 0.800≤P'<1.000), typically, after calculating P', further omitting the figures of the fourth decimal place and under of P', Q'=(P'-([P']+1))×1000 is calculated. In this case, it becomes P'-([P']+1)=1.XYZ-([1.XYZ]+1)=1.XYZ-2. Accordingly, it becomes Q'=(P'-([P']+1))×1000=(1.XYZ-2)×1000, and becomes integers equal to or larger than −1000 and equal to or less than −1. As an example, in case of P'=0.912, it becomes Q'=(P'-([P']+1))×1000=(0.912-([0.912]+1))×1000=(0.912-1)×1000=−0.088×1000=−88.

The method of calculating the index for deciding the necessity of surgically operating on the jaw is executed by a computer comprising the predetermined programs including equations of P' and Q'. The programs can be stored in various kinds of computer readable recording media such as CD-ROMs, etc., for example, or can be provided through the telecommunications lines such as the Internet, etc. As necessary, data for calculation, for example, the distances (S-A), (S-N), (S-B) and (Go-Me) in the cephalometric radiogram are entered into the computer. Or, for example, the image data obtained by cephalometric radiography is put in to a computer, from the image data, the coordinates of S, A, N, B, Go and Me are measured, from the coordinates measured by this, the distances (S-A), (S-N), (S-B) and (Go-Me) are obtained by calculations, P' and Q' may be calculated according to the equations using the distances.

Also, the method of deciding the necessity of surgically operating on the jaw can be executed by a computer using the predetermined programs including equations of P' and Q' and equations for decision of P' and Q'. These programs can be stored in various kinds of computer readable recording media such as CD-ROMs, etc., for example, or can be provided through the telecommunications lines such as the Internet, etc. The necessary data for the calculation can be obtained as the same as the method of calculating the index for deciding the necessity of surgically operating on the jaw.

According to the fifth aspect of the present invention, there is a method provided of calculating an index for deciding disharmony of the maxilla and mandible in dental treatment, comprising a step of:

calculating P=((S-B)+(Go-Me))/(S-A) using the distance (S-A) between S and A, the distance (S-B) between S and B and the distance (Go-Me) between Go and Me which are measured by cephalometric radiography of a patient.

According to the sixth aspect of the present invention, there is a method provided of deciding disharmony of the maxilla and mandible in dental treatment, comprising steps of:

calculating P=((S-B)+(Go-Me))/(S-A) using the distance (S-A) between S and A, the distance (S-B) between S and B and the distance (Go-Me) between Go and Me which are measured by cephalometric radiography of a patient, or further omitting the figures of the fourth decimal place and under of P, and calculating $$Q=(P-[P])\times1000 \text{ ([ ] denotes Gauss's symbol) (where } 2.000 \leq P<3.000)$$

or $$Q=(P-([P]+1))\times1000 \text{ ([ ] denotes Gauss's symbol) (where } P<2.000), \text{ and}$$

deciding disharmony of the maxilla and mandible by deciding whether calculated P or Q is equal to or larger than the predetermined value or not, respectively.

The method of calculating the index for deciding disharmony of the maxilla and mandible can be executed by a computer comprising the predetermined programs including the equations of P and Q. The programs can be stored in various kinds of computer readable recording media such as CD-ROMs, etc., for example, or can be provided through the telecommunications lines such as the Internet, etc. The necessary data for the calculations can be obtained in the same way as the method of calculating the index for deciding the necessity of surgically operating on the jaw.

Also, the method of deciding disharmony of the maxilla and mandible can be executed by a computer comprising the predetermined programs including equations of P and Q or equations for decision of P and Q. The programs can be stored in various kinds of computer readable recording media such as CD-ROMs, etc., for example, or can be provided through the telecommunications lines such as the Internet, etc. The necessary data for the calculations can be obtained in the same way as the method of deciding the necessity of surgically operating on the jaw.

According to the seventh aspect of the present invention, there is a method provided of calculating an index for deciding disharmony of the maxilla and mandible in dental treatment, comprising a step of:

calculating P'=((S-B)+(Go-Me))/((S-A)+(S-N)) using the distance (S-A) between S and A, the distance (S-N) between S and N, the distance (S-B) between S and B and the distance (Go-Me) between Go and Me which are measured by cephalometric radiography of a patient.

According to the eighth aspect of the present invention, there is a method provided of deciding disharmony of the maxilla and mandible in dental treatment, comprising steps of:

calculating P'=((S-B)+(Go-Me))/((S-A)+(S-N)) using the distance (S-A) between S and A, the distance (S-N) between S and N, the distance (S-B) between S and B and the distance (Go-Me) between Go and Me which are measured by cephalometric radiography of a patient, or further omitting the figures of the fourth decimal place and under of P', and calculating $$Q'=(P'-[P'])\times1000 \text{ ([ ] denotes Gauss's symbol) (where } 1.000 \leq P<2.000),$$

or $$Q'=(P'-([P']+1))\times1000 \text{ ([ ] denotes Gauss's symbol) (where } P'<1.000), \text{ and}$$

deciding disharmony of the maxilla and mandible by deciding whether calculated P' or Q' is equal to or larger than the predetermined value or not, respectively.

The method of calculating the index for deciding disharmony of the maxilla and mandible can be executed by a computer comprising the predetermined programs including equations of P' and Q'. The programs can be stored in various kinds of computer readable recording media such as CD-ROMs, etc., for example, or can be provided through the telecommunications lines such as the Internet, etc. The necessary data for the calculation can be obtained as the same as the method of calculating the index for deciding the necessity of surgically operating on the jaw.

Also, the method of deciding disharmony of the maxilla and mandible can be executed by a computer comprising the predetermined programs including equations of P' and Q' or equations for decision of P' and Q'. The programs can be stored in various kinds of computer readable recording media such as CD-ROMs, etc., for example, or can be provided through the telecommunications lines such as the Internet, etc. The necessary data for the calculations can be obtained as the same as the method of deciding the necessity of surgically operating on the jaw.

Here, the dental treatment includes various kinds of treatments which are effective to treat according to disharmony of the maxilla and mandible, specifically, for example, other than orthodontic treatment, also includes prosthesis such as artificial teeth (false teeth), etc. In the method of calculating the index for deciding disharmony of the maxilla and mandible and the method of deciding disharmony of the maxilla and mandible, unless contrary to the nature, the explanation of the method of calculating the index for deciding the necessity of surgically operating on the jaw and the method of deciding the necessity of surgically operating on the jaw come into effect.

According to the ninth aspect of the present invention, there is a method provided of calculating an index for deciding dentofacial deformity, comprising a step of:

Calculating P=((S-B)+(Go-Me))/(S-A) using the distance (S-A) between S and A, the distance (S-B) between S and B and the distance (Go-Me) between Go and Me which are measured by cephalometric radiography of a patient.

According to the tenth aspect of the present invention, there is a method provided of deciding dentofacial deformity, comprising steps of:

calculating P=((S-B)+(Go-Me))/(S-A) using the distance (S-A) between S and A, the distance (S-B) between S and B and the distance (Go-Me) between Go and Me which are measured by cephalometric radiography of a patient, or further omitting the figures of the fourth decimal place and under of P, and calculating $$Q=(P-[P])\times1000 \text{ ([ ] denotes Gauss's symbol) (where } 2.000 \leq P<3.000)$$

or $$Q=(P-([P]+1))\times1000 \text{ ([ ] denotes Gauss's symbol) (where } P<2.000); \text{ and}$$

deciding whether the patient suffers from dentofacial deformity by deciding whether calculated P or Q is equal to or larger than the predetermined value or not, respectively.

The method of calculating the index for deciding dentofacial deformity can be executed by a computer comprising the predetermined programs including the equations of P and Q. The programs can be stored in various kinds of computer readable recording media such as CD-ROMs, etc., for example, or can be provided through the telecommunications lines such as the Internet, etc. The necessary data for the calculations can be obtained as the same as the method of calculating the index for deciding the necessity of surgically operating on the jaw.

Also, the method of deciding dentofacial deformity can be executed by a computer comprising the predetermined programs including equations of P and Q or equations for decision of P and Q. The programs can be stored in various kinds of computer readable recording media such as CD-ROMs, etc., for example, or can be provided through the telecommunications lines such as the Internet, etc. The necessary data for the calculations can be obtained in the same way as the method of deciding the necessity of surgically operating on the jaw.

According to the eleventh aspect of the present invention, there is a method provided of calculating an index for deciding dentofacial deformity, comprising a step of:

calculating $P'=((S-B)+(Go-Me))/((S-A)+(S-N))$ using the distance (S-A) between S and A, the distance (S-N) between S and N, the distance (S-B) between S and B and the distance (Go-Me) between Go and Me which are measured by cephalometric radiography of a patient.

According to the twelfth aspect of the present invention, there is a method provided of deciding dentofacial deformity, comprising steps of:

calculating $P'=((S-B)+(Go-Me))/((S-A)+(S-N))$ using the distance (S-A) between S and A, the distance (S-N) between S and N, the distance (S-B) between S and B and the distance (Go-Me) between Go and Me which are measured by cephalometric radiography of a patient, or further omitting the figures of the fourth decimal place and under of P', and calculating $Q'=(P'-[P'])\times1000$ ([ ] denotes Gauss's symbol)
(where $1.000 \leq P' < 2.000$), or $Q'=(P'-([P']+1))\times1000$ ([ ] denotes Gauss's symbol)
(where $P'<1.000$); and deciding whether the patient suffers from dentofacial deformity by deciding whether calculated P' or Q' is equal to or larger than the predetermined value or not, respectively.

The method of calculating the index for deciding dentofacial deformity can be executed by a computer comprising the predetermined programs including equations of P' and Q'. The programs can be stored in various kinds of computer readable recording media such as CD-ROMs, etc., for example, or can be provided through the telecommunications lines such as the Internet, etc. The necessary data for the calculation can be obtained in the same way as the method of calculating the index for deciding the necessity of surgically operating on the jaw. Also, the method of deciding dentofacial deformity can be executed by a computer comprising the predetermined programs including equations of P' and Q' or equations for decision of P' and Q'. The programs can be stored in various kinds of computer readable recording media such as CD-ROMs, etc., for example, or can be provided through the telecommunications lines such as the Internet, etc. The necessary data for the calculations can be obtained in the same way as the method of deciding the necessity of surgically operating on the jaw.

According to embodiments of the present invention, in orthodontic treatment of a patient, an index may be calculated for deciding the necessity of surgically operating on the jaw, which becomes an objective criterion to decide the necessity of surgically operating on the jaw of the patient, and by appropriately combining the results of other inspection methods, the dentist may be able to make a correct diagnosis with higher objectivity and more easily, moreover within a short period of time. Also, in the dental treatment such as orthodontic treatment, etc. of a patient, an index may be calculated for deciding disharmony of the maxilla and mandible, which becomes an objective criterion to decide disharmony of the maxilla and mandible of the patient, and by appropriately combining the results of other inspection methods, the dentist may be able to make a correct diagnosis more easily with higher objectivity, moreover within a short period of time. Also, an index may be calculated for deciding dentofacial deformity, which becomes an objective criterion to decide whether a patient suffers from dentofacial deformity or not, and by appropriately combining the results of other inspection methods, the doctor or the dentist may be able to make a correct diagnosis more easily with higher objectivity, moreover within a short period of time.

DETAILED DESCRIPTION

Embodiments of the invention will now be explained below with reference to the drawings.

First explained is the first embodiment.

In the first embodiment, a method of calculating an OPE index as an index for deciding the necessity of surgically operating on the jaw in orthodontic treatment is explained.

Figure 1:
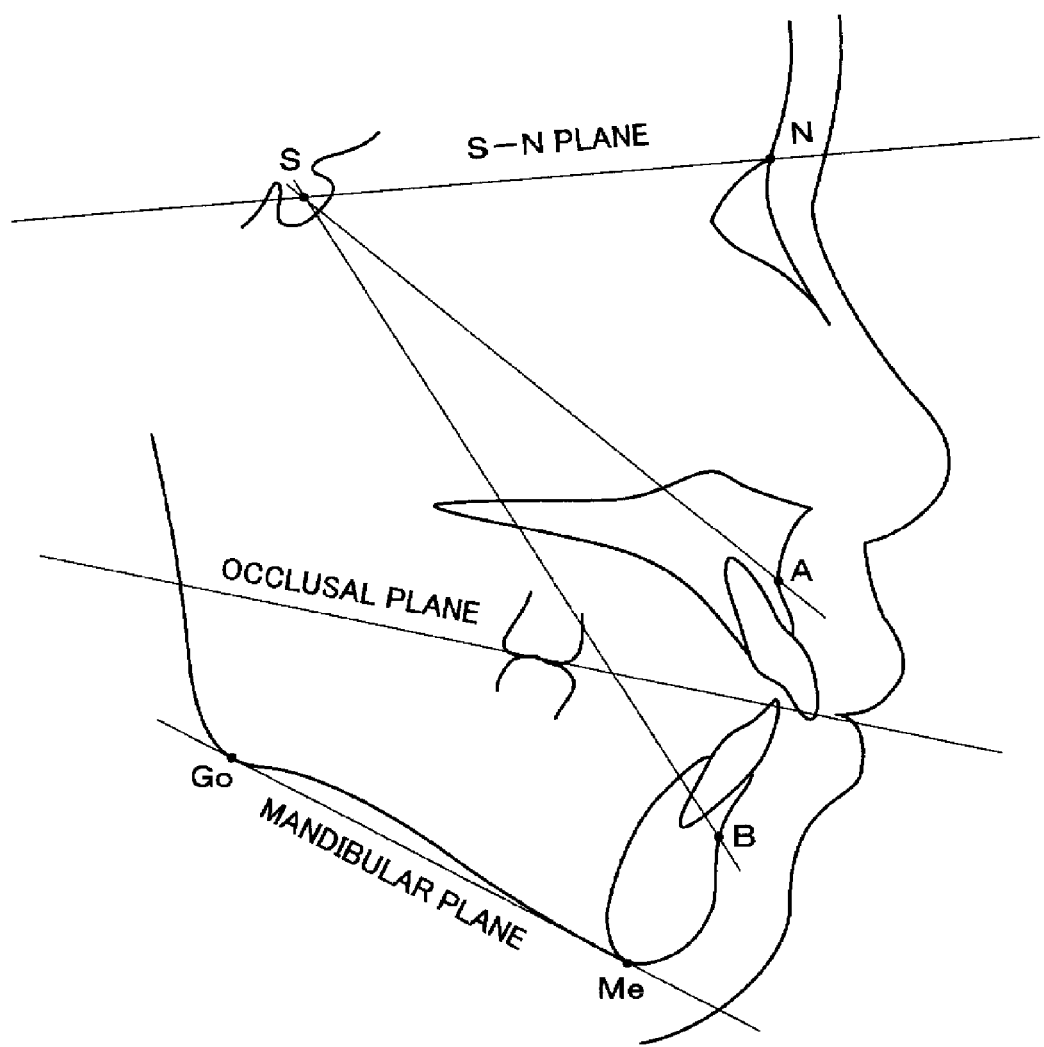
FIG. 1 is a schematic drawing for explaining the measured points in a cephalometric radiogram.
Figure 2:
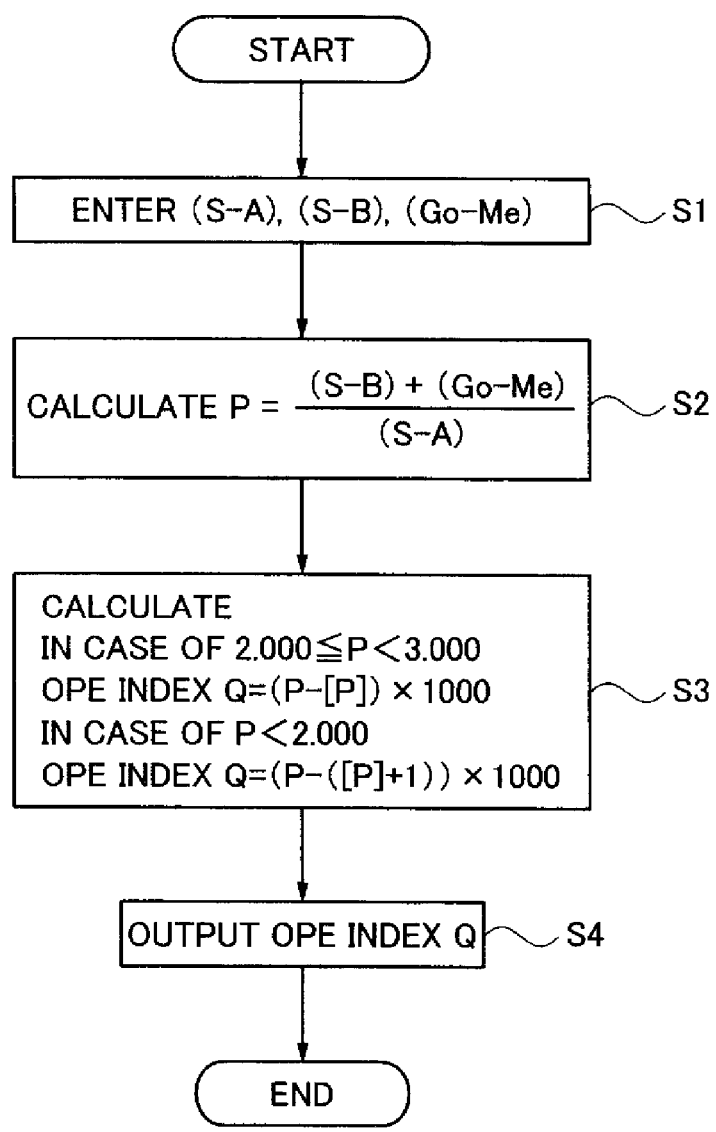
FIG. 2 is a flowchart showing a method of calculating an index for deciding the necessity of surgically operating on the jaw in orthodontic treatment according to the first embodiment of the present invention.

FIG. 2 shows a flowchart of a method of calculation. Programs are created according to the flowchart, and are executed on a computer.

Before making the calculation, taking a cephalometric radiogram of a patient to be treated orthodontic treatment, the distance (S-A) between S and A, the distance (S-B) between S and B and the distance (Go-Me) between Go and Me are measured. The measurement of the distances can be executed by entering the coordinate data of measured points of S, A, B, Go and Me on the cephalometric radiogram, for example, by using a pen tablet or a digitizer. Or, by scanning the image data obtained by cephalometric radiography to a computer, and measuring the coordinates of S, A, B, Go and Me from the image data, the distances (S-A), (S-B) and (Go-Me) may be obtained by calculations from the measured coordinates.

As shown in FIG. 2, in step S1, the distances (S-A), (S-B) and (Go-Me) which are measured by the above are entered.

In step S2, from the entered distances (S-A), (S-B) and (Go-Me), P is calculated according to $$P=((S-B)+(Go-Me))/(S-A).$$

In the step S3, omitting the figures of the fourth decimal place and under of P obtained by the above calculation, and in case of $2.000 \leq P < 3.000$, calculating an OPE index Q according to $Q=(P-[P]) \times 1000$, and in case of $P<2.000$, calculating an OPE index Q according to $Q=(P-([P]+1)) \times 1000$.

In step S4, the OPE index Q calculated as the above is output on a display, for example.

In the case that the OPE index Q calculated like this is equal to or larger than 400, in orthodontic treatment, it can be diagnosed that the surgical application, in other words, the surgical operation on the jaw, typically the severing operation on the mandible is necessary. Also, in case that the OPE index Q is equal to or larger than 350 or less than 400, which is a borderline case, by the distance (S-N) and Wits analysis, a supplementary analysis is added. In case that the distance (S-N) is shorter than over 2SD than the average, when the result of Wits analysis is equal to or larger than 12 mm, it is decided that the surgical application, in other words, the surgical operation of the jaw is necessary.

In case that the OPE index Q is less than 350, equal to or larger than 0, in orthodontic treatment, it can be decided that the surgical operation on the jaw is not necessary.

Also, in the case that the OPE index Q is negative, meaning a high retrograde growth tendency (bradyauxesis) of the mandible or an overgrowth (tachyauxesis) tendency of the maxilla, it is necessary to consider the surgical operation on the jaw. Generally, in the case that the OPE index Q is equal to or larger than −50, and less than 0, the necessity of the surgical operation on the jaw becomes high.

Generally, in addition to the OPE index Q, a dentist finally decides the necessity of surgically operating on the jaw by combining the results of other inspections, such as conventional cephalometric analysis, etc., and focusing mainly on the angle measurement.

EXAMPLE 1

Figure 3:
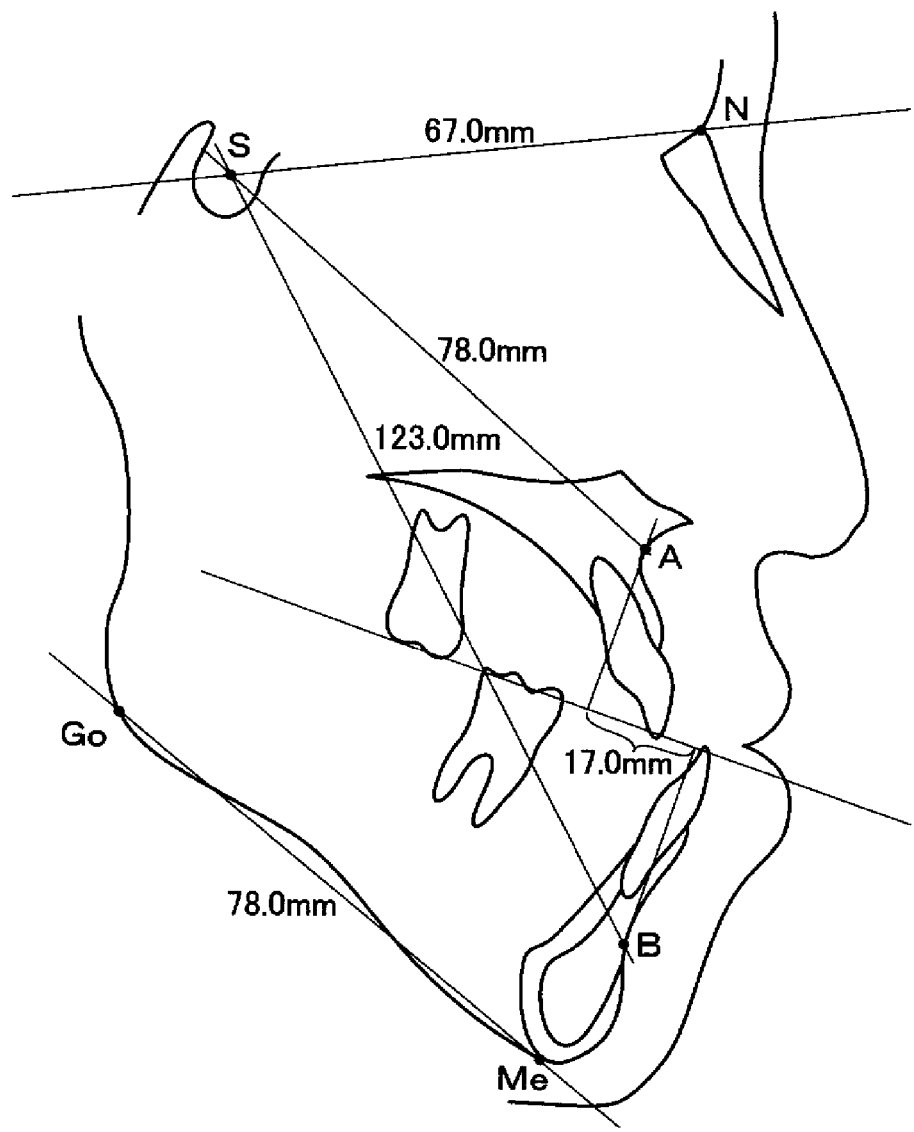
FIG. 3 is a tracing made based on a cephalometric radiogram of a patient 1.

A cephalometric radiogram of patient 1 was taken. FIG. 3 shows a tracing made based on the cephalometric radiogram.

From FIG. 3, the distances (S-A), (S-B) and (Go-Me) were measured. The results are: (S-A)=78.0 mm, (S-B)=123.0 mm and (Go-Me)=78.0 mm. Using the data, the calculation of P is given as follows: (123.0+78.0)/78.0=2.576. Therefore, the OPE index Q is 576. This means that the disharmony of the maxilla and mandible is very large, and patient 1 suffers from dentofacial deformity. In this case, (S-N)=67.0 mm and Wits=17.0 mm.

As the OPE index Q is 576, it can be decided that the severing operation on the mandible is necessary for orthodontic treatment.

Therefore, the severing operation on the mandible was performed. After the severing operation, a cephalometric radiogram of the patient 1 was taken. A tracing made based on the cephalometric radiogram is shown in FIG. 4.

Figure 4:
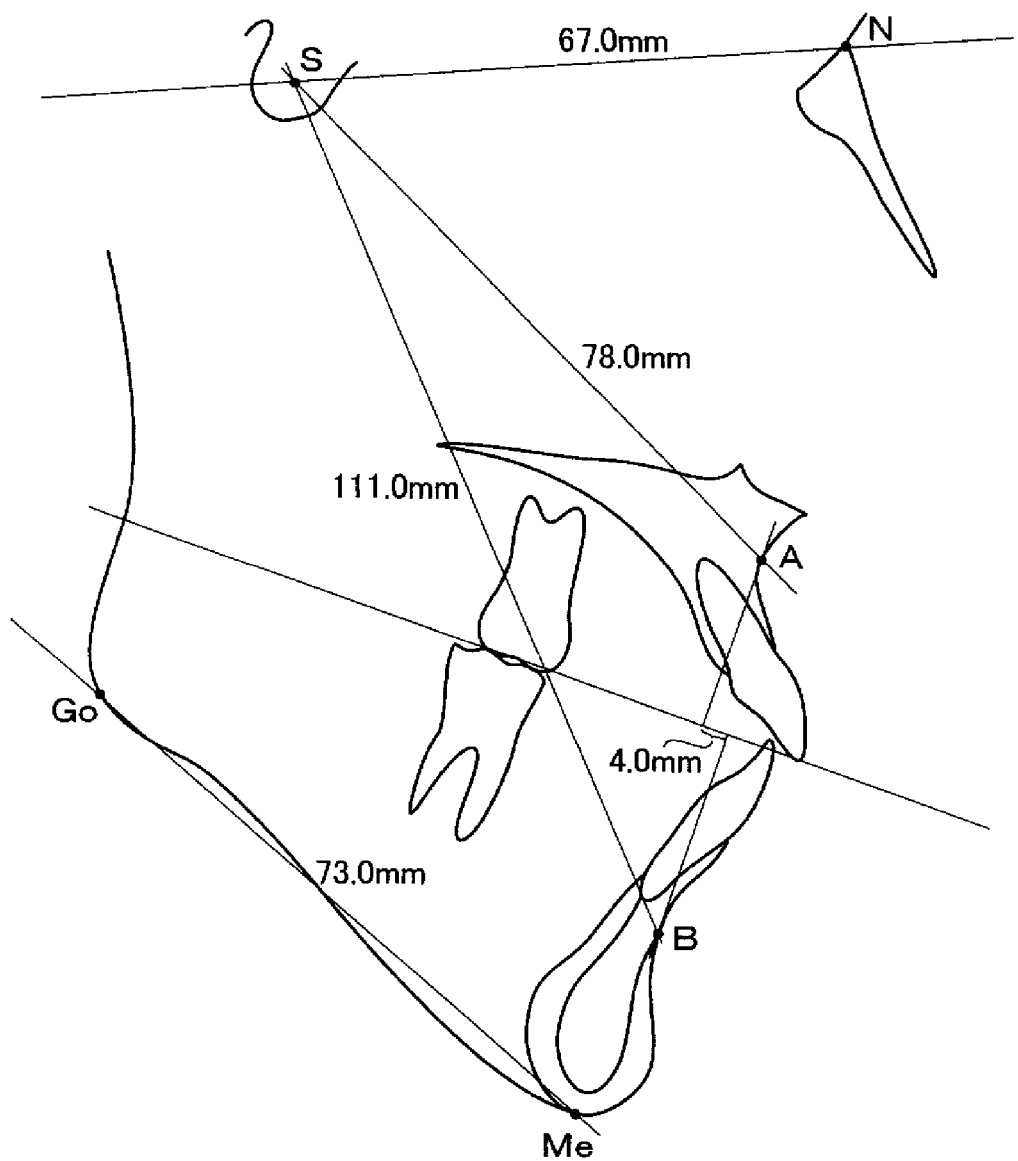
FIG. 4 is a tracing made based on a cephalometric radiogram taken after the severing operation on the mandible of the patient 1.

From FIG. 4, the distances (S-A), (S-B) and (Go-Me) were measured. The results are: (S-A)=78.0 mm, (S-B)=111.0 mm and (Go-Me)=73.0 mm. Using the data, the calculation of P is given as follows: (111.0+73.0)/78.0=2.358. Therefore, the OPE index Q is 358. This means that the disharmony of the maxilla and mandible was improved and patient 1 does not suffer from dentofacial deformity. In this case, (S-N)=67.0 mm and Wits=4.0 mm.

As the OPE index Q is 358, it can be decided that patient 1 able to be treated by orthodontic treatment from the results of the severing operation on the mandible.

EXAMPLE 2

A cephalometric radiogram of patient 2 was taken. A tracing made based on the cephalometric radiogram is shown in FIG. 5.

Figure 5:
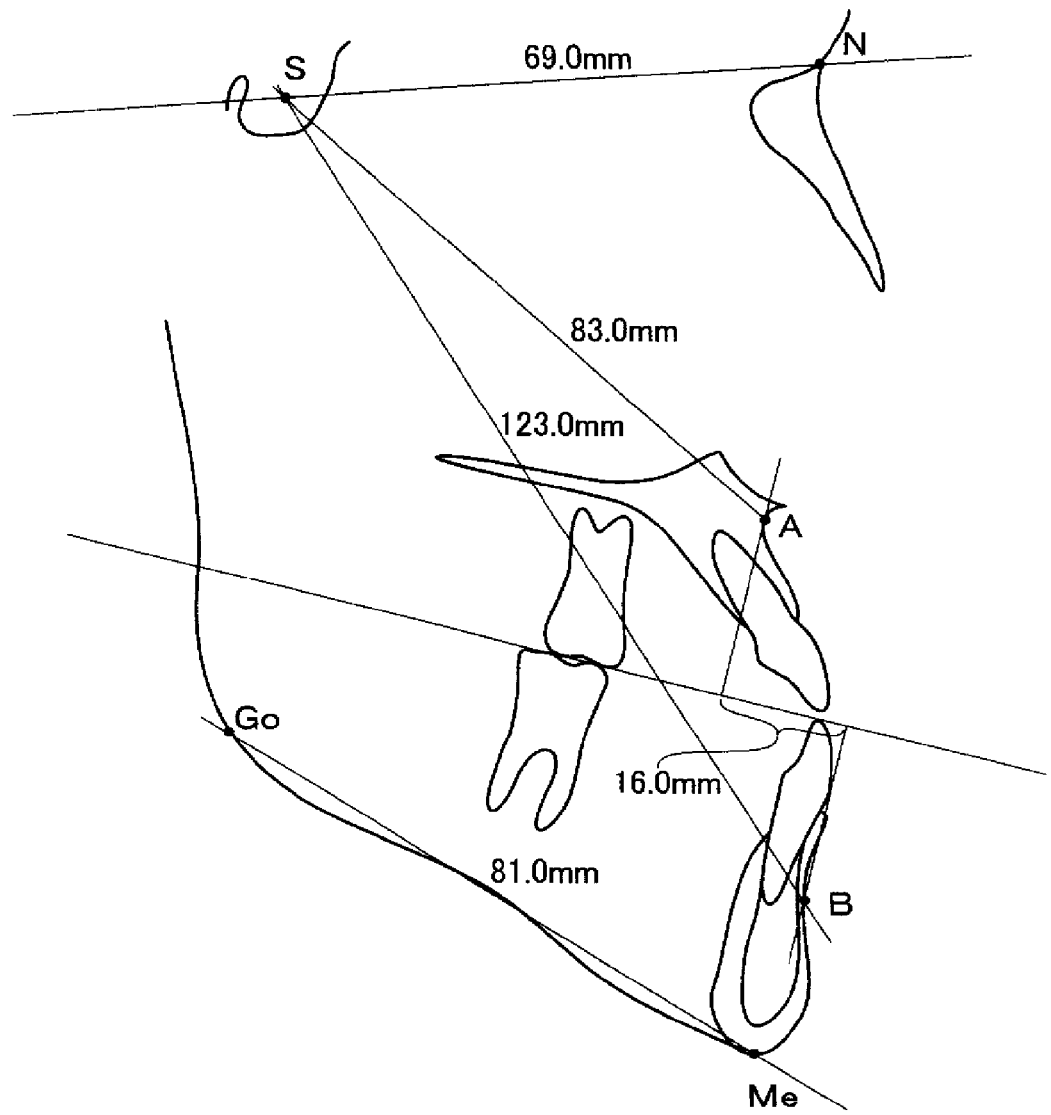
FIG. 5 is a tracing made based on a cephalometric radiogram of a patient 2.

From FIG. 5, the distances (S-A), (S-B) and (Go-Me) were measured. The results are: (S-A)=83.0 mm, (S-B)=123.0 mm and (Go-Me)=81.0 mm. Using the data, the calculation of P is given as follows: (123.0+81.0)/83.0=2.457. Therefore, the OPE index Q is 457. This means that the disharmony of the maxilla and mandible is very large and patient 2 suffers from dentofacial deformity. In this case, (S-N)=69.0 mm and Wits=16.0 mm.

As the OPE index Q 457, it can be decided that patient 2 needs the severing operation on the mandible.

Therefore, the necessary severing operation on the mandible was performed. After the severing operation, a cephalometric radiogram of the patient 2 was taken. A tracing made based on the cephalometric radiogram is shown in FIG. 6.

Figure 6:
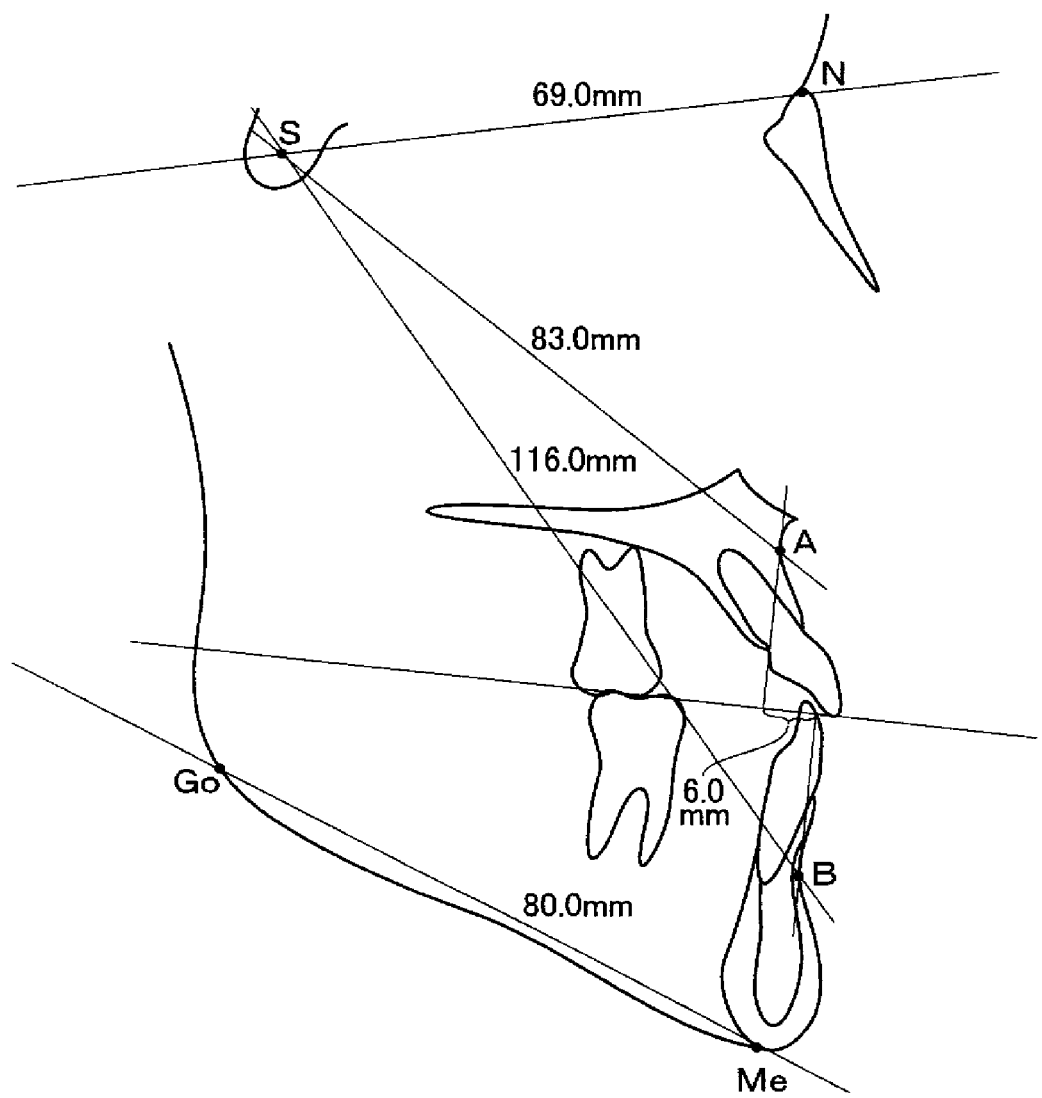
FIG. 6 is a tracing made based on a cephalometric radiogram taken after the severing operation on the mandible of the patient 2.

From FIG. 6, the distances (S-A), (S-B) and (Go-Me) were measured. The results are: (S-A)=83.0 mm, (S-B)=116.0 mm and (Go-Me)=80.0 mm. Using the data, the calculation of P is given as follows: (116.0+80.0)/83.0=2.361. Therefore, the OPE index Q is 361. This means that the disharmony of the maxilla and mandible was improved and patient 2 does not suffer from dentofacial deformity. In this case, (S-N)=69.0 mm and Wits=6.0 mm.

As the OPE index Q 361, it decided that patient 2 was able to be treated by orthodontic treatment from the results of the severing operation on the mandible.

EXAMPLE 3

A cephalometric radiogram of patient 3 was taken. A tracing made based on the cephalometric radiogram is shown in FIG. 7.

Figure 7:
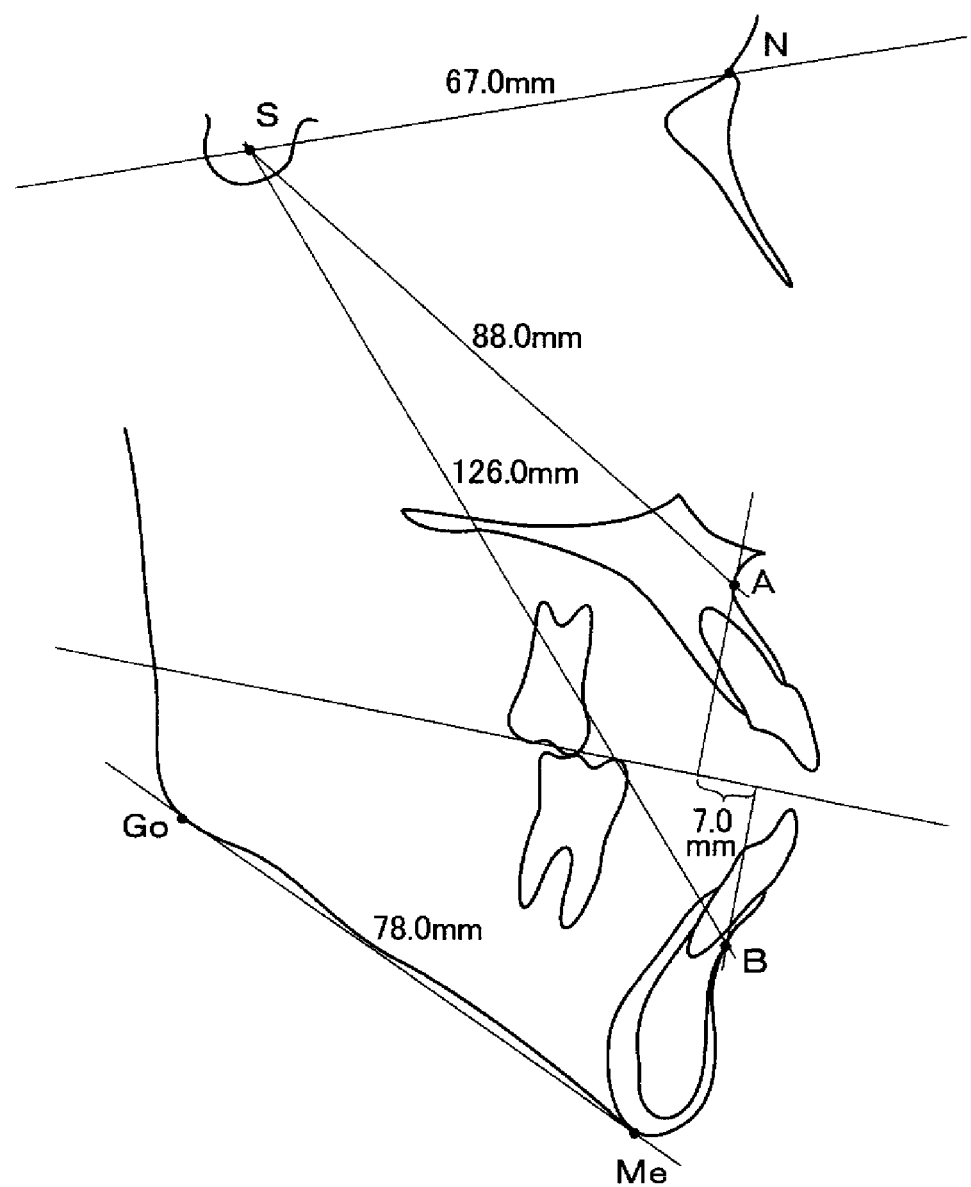
FIG. 7 is a tracing made based on a cephalometric radiogram of a patient 3.

From FIG. 7, the distances (S-A), (S-B) and (Go-Me) were measured. The results are: (S-A)=88.0 mm, (S-B)=126.0 mm and (Go-Me)=78.0 mm. Using the data, the calculation of P is given as follows: (126.0+78.0)/88.0=2.318. Therefore, the OPE index Q is 318. In this case, (S-N)=67.0 mm and Wits=7.0 mm.

It is a case of light skeletal Class III, however, as the OPE index Q was 318, it can be decided that the patient 3 not need to have the jaw operated on at the time of performing orthodontic treatment.

EXAMPLE 4

A cephalometric radiogram of patient 4 was taken. A tracing made based on the cephalometric radiogram is shown in FIG. 8.

Figure 8:
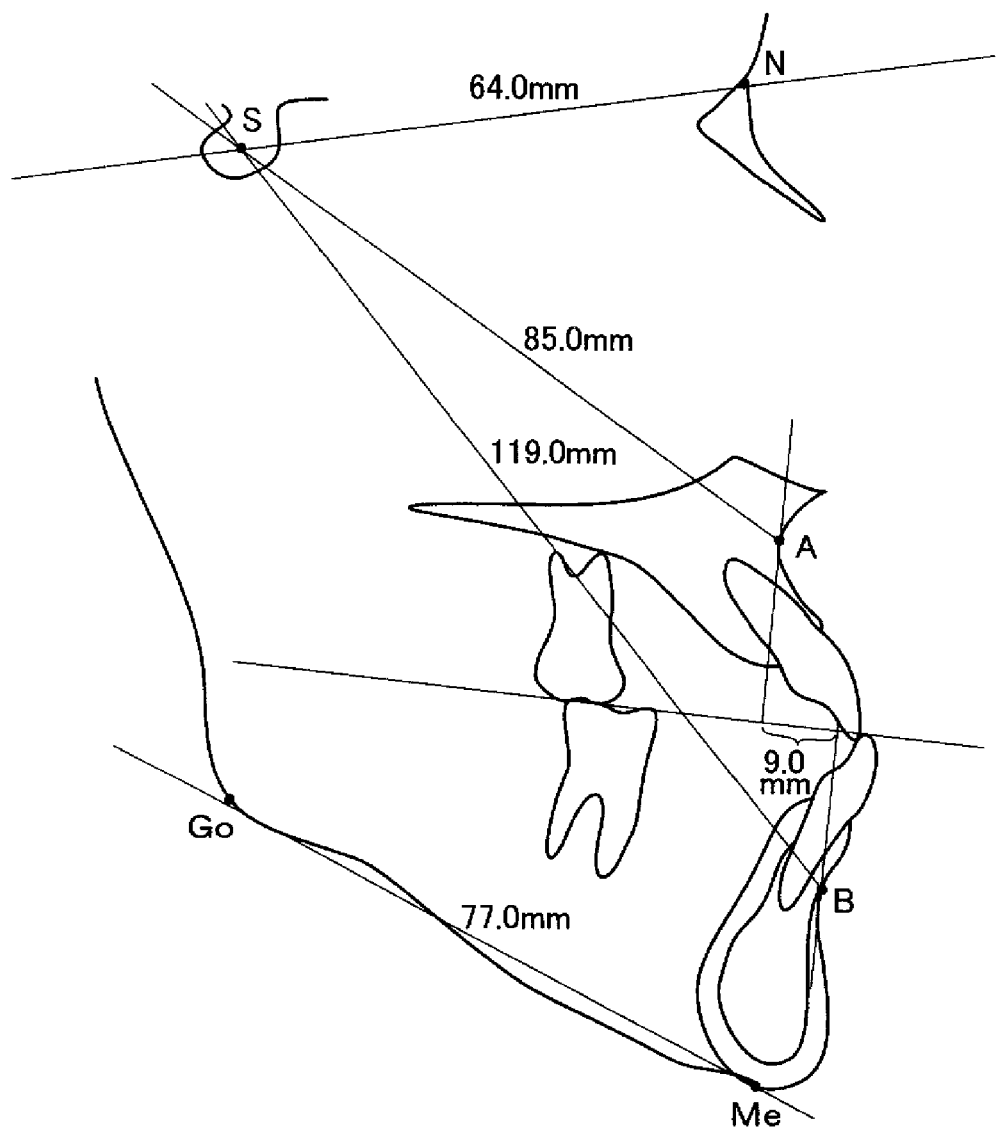
FIG. 8 is a tracing made based on a cephalometric radiogram of a patient 4.

From FIG. 8, the distances (S-A), (S-B) and (Go-Me) were measured. The results are: (S-A)=85.0 mm, (S-B)=119.0 mm and (Go-Me)=77.0 mm. Using the data, the calculation of P is given as follows: (119.0+77.0)/85.0=2.305. Therefore, the OPE index Q is 305. In this case, (S-N)=64.0 mm and Wits=9.0 mm.

It is a case of skeletal Class III, however, as the OPE index Q 305, it can be decided that patient 4 does not need to have the jaw operated on at the time of performing orthodontic treatment.

EXAMPLE 5

A cephalometric radiogram of patient 5 was taken. A tracing made based on the cephalometric radiogram is shown in FIG. 9.

Figure 9:
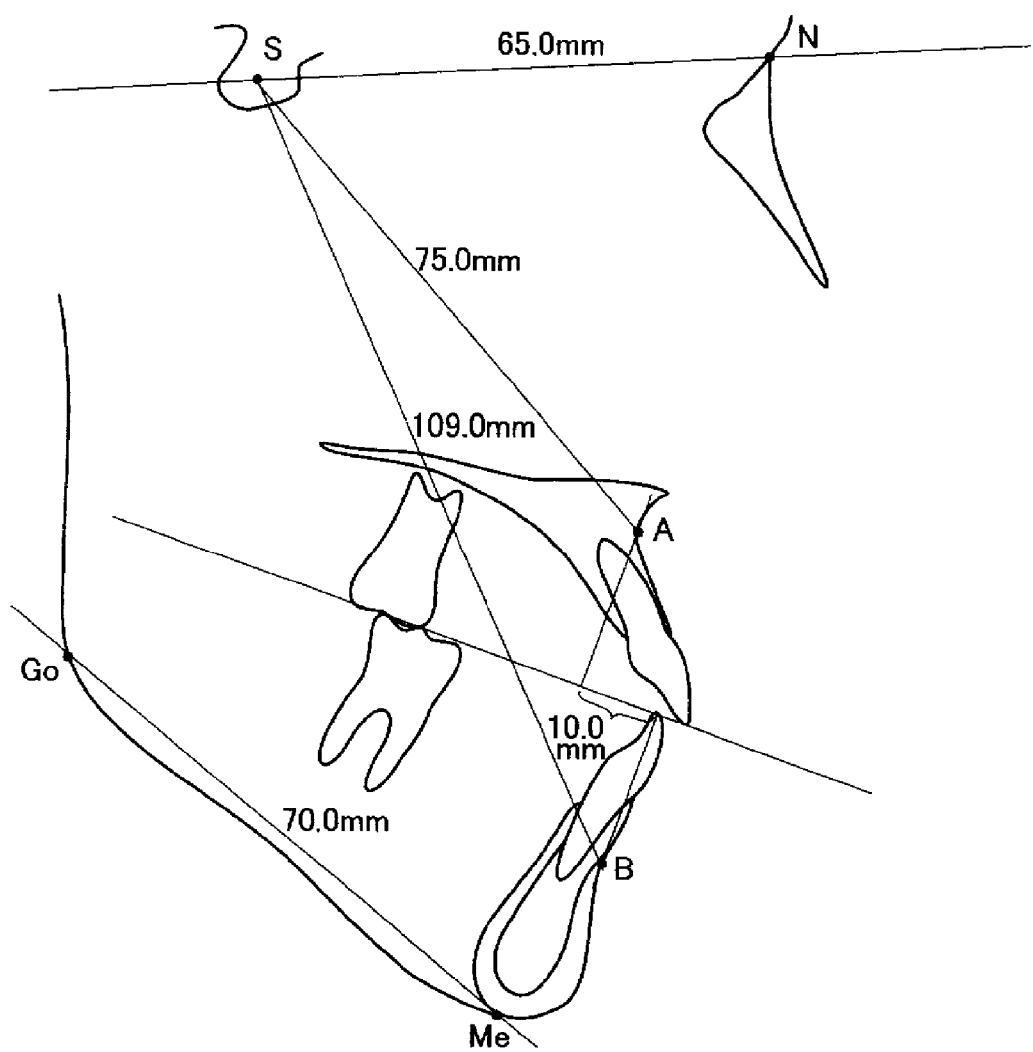
FIG. 9 is a tracing made based on a cephalometric radiogram of a patient 5.

From FIG. 9, the distances (S-A), (S-B) and (Go-Me) were measured. The results are: (S-A)=75.0 mm, (S-B)=109.0 mm and (Go-Me)=70.0 mm. Using the data, the calculation of P is given as follows: (109.0+70.0)/75.0=2.386. Therefore, the OPE index Q is 386. In this case, (S-N)=65.0 mm and Wits=10.0 mm.

As the OPE index Q is 386, it is a borderline case. As Wits is 10.0 mm, it is quite a skeletally strong case, but with (S-N)=65.0 mm, it can be decided that the operation on the jaw is not needed at the time of performing orthodontic treatment.

EXAMPLE 6

A cephalometric radiogram of patient 6 was taken. A tracing made based on the cephalometric radiogram is shown in FIG. 10.

Figure 10:
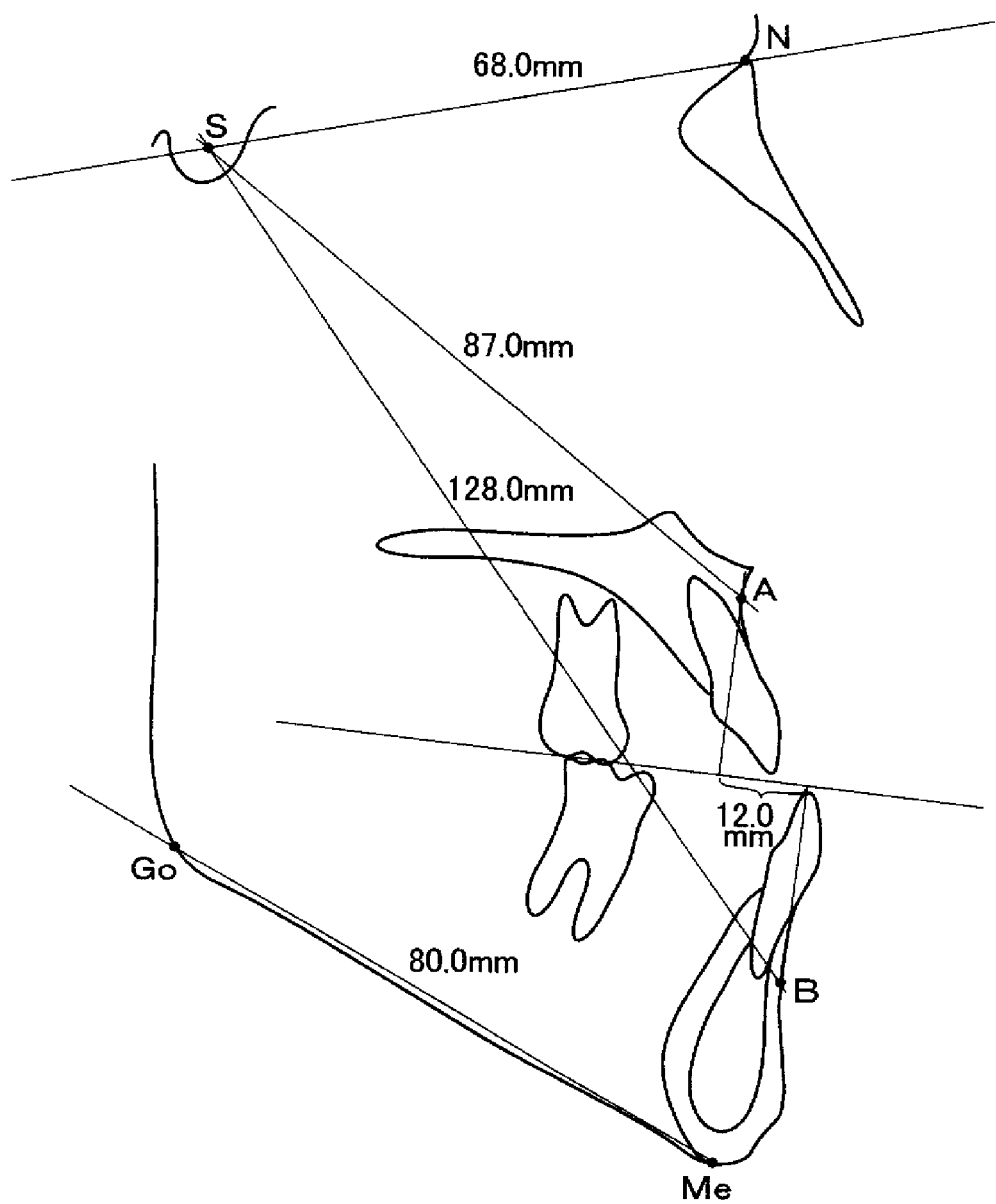
FIG. 10 is a tracing made based on a cephalometric radiogram of a patient 6.

From FIG. 10, the distances (S-A), (S-B) and (Go-Me) were measured. The results are: (S-A)=87.0 mm, (S-B)=128.0 mm and (Go-Me)=80.0 mm. Using the data, the calculation of P is given as follows: (128.0+80.0)/87.0=2.390. Therefore, the OPE index Q is 390. In this case, (S-N)=68.0 mm and Wits=12.0 mm.

As the OPE index Q is 390, it a borderline case. The Wits 12.0 mm, which is larger than 10.0 mm, also, with (S-N)=68.0 mm, it can be decided to be a case of skeletal Class III, and patient 6 suffers from dentofacial deformity, and it can be decided that the severing operation on the mandible is necessary.

Therefore, the necessary severing operation on the mandible was performed. After the severing operation, a cephalometric radiogram of patient 6 was taken. A tracing made based on the cephalometric radiogram is shown in FIG. 11.

Figure 11:
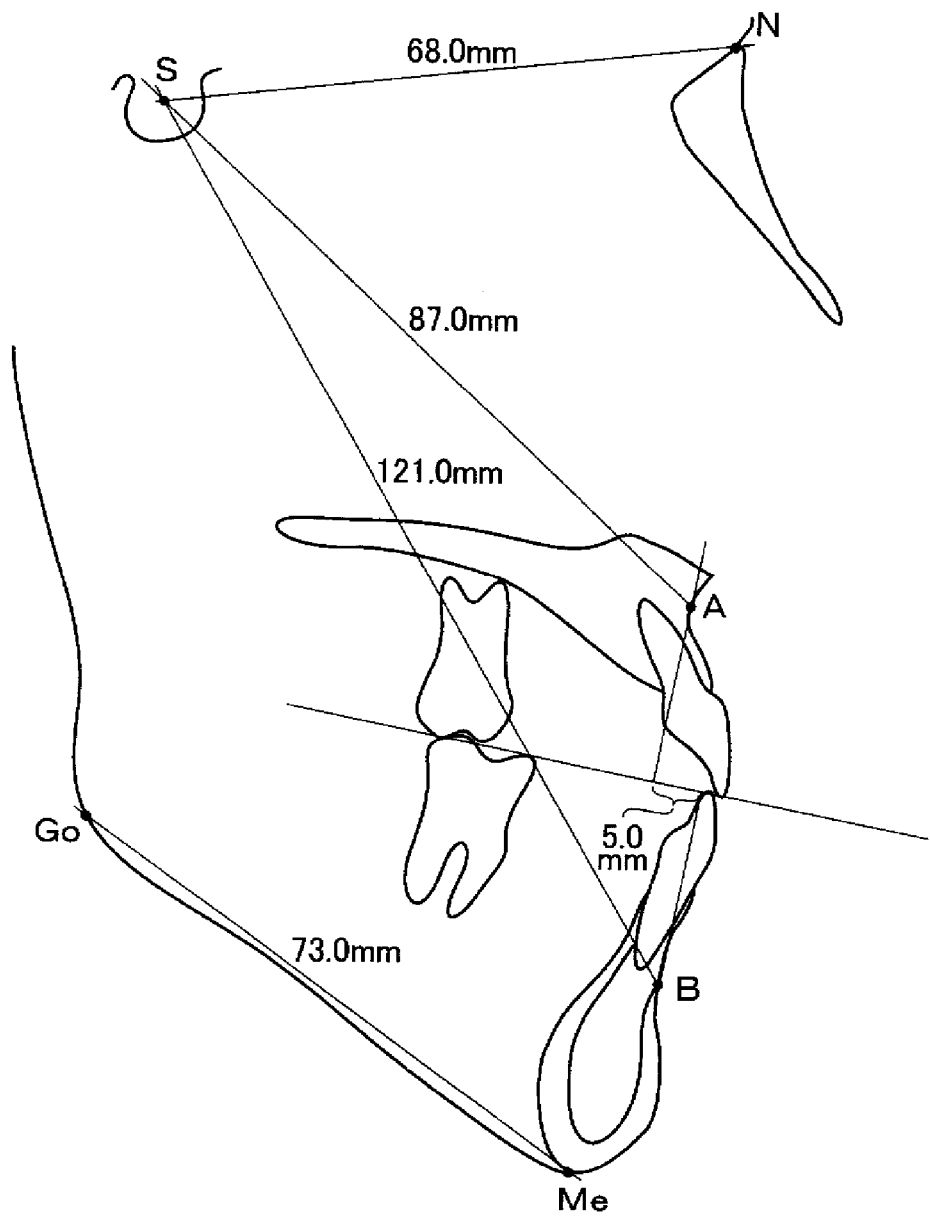
FIG. 11 is a tracing made based on a cephalometric radiogram taken after severing operation on the mandible of the patient 6.

From FIG. 11, the distances (S-A), (S-B) and (Go-Me) were measured. The results are: (S-A)=87.0 mm, (S-B)=121.0 mm and (Go-Me)=73.0 mm. Using the data, the calculation of P is given as follows: (121.0+73.0)/87.0=2.229. Therefore, the OPE index Q is 229. In this case, (S-N)=68.0 mm and Wits=5.0 mm.

As the OPE index Q is 229, it can be decided that patient 6 is able to be treated by orthodontic treatment from the results of the severing operation on the mandible.

EXAMPLE 7

A cephalometric radiogram of patient 7 was taken. A tracing made based on the cephalometric radiogram is shown in FIG. 12.

Figure 12:
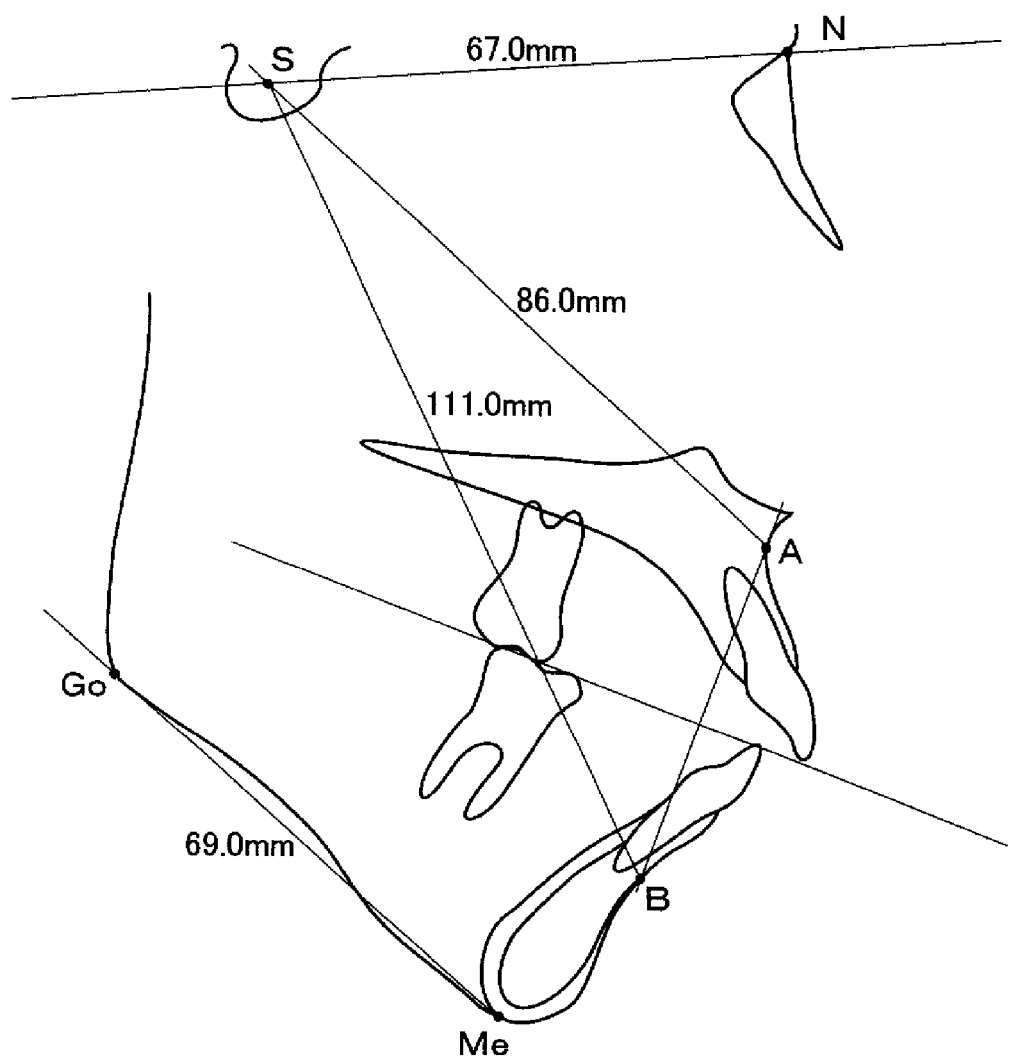
FIG. 12 is a tracing made based on a cephalometric radiogram of a patient 7.

From FIG. 12, the distances (S-A), (S-B) and (Go-Me) were measured. The results are: (S-A)=86.0 mm, (S-B)=111.0 mm and (Go-Me)=69.0 mm. Using the data, the calculation of P is given as follows: (111.0+69.0)/86.0=2.093. Therefore, the OPE index Q is 93. In this case, (S-N)=67.0 mm and Wits=0 mm.

The OPE index Q is 93, and there a retrograde growth tendency of the mandible, but it can be decided that the patient 7 does not need to have the jaw operated on at the time of performing orthodontic treatment, and an orthodontic treatment of a tooth extraction is applied.

EXAMPLE 8

A cephalometric radiogram of patient 8 was taken. A tracing made based on the cephalometric radiogram is shown in FIG. 13.

Figure 13:
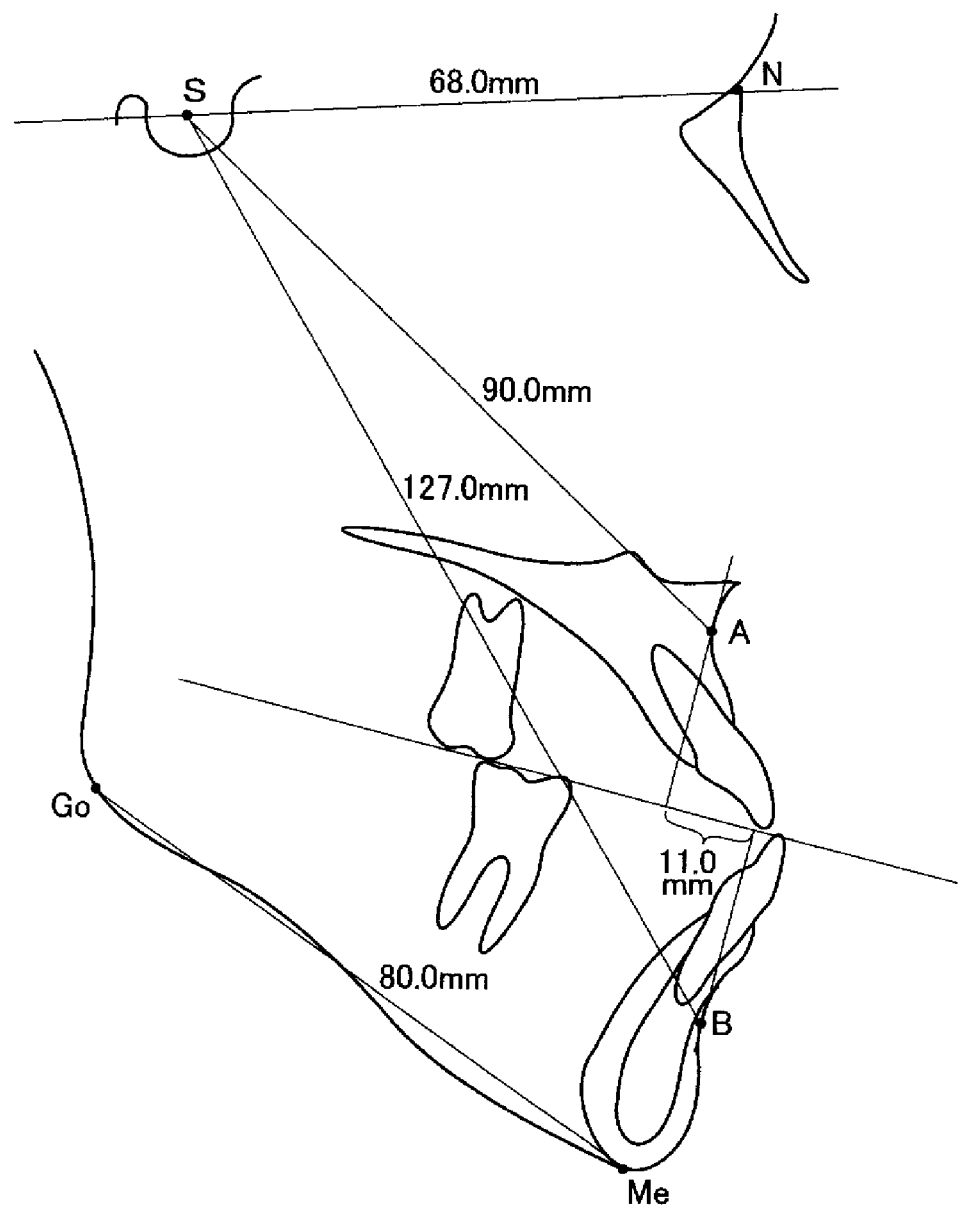
FIG. 13 is a tracing made based on a cephalometric radiogram of a patient 8.

From FIG. 13, the distances (S-A), (S-B) and (Go-Me) were measured. The results are: (S-A)=90.0 mm, (S-B)=127.0 mm and (Go-Me)=80.0 mm. Using the data, the calculation of P is given as follows: (127.0+80.0)/90.0=2.300. Therefore, the OPE index Q is 300. In this case, (S-N)=68.0 mm and Wits=11.0 mm.

As the OPE index Q is 300, it can be judged that patient 8 does not need to have the jaw operated on at the time of performing orthodontic treatment.

EXAMPLE 9

A cephalometric radiogram of patient 9 was taken. A tracing made based on the cephalometric radiogram is shown in FIG. 14.

Figure 14:
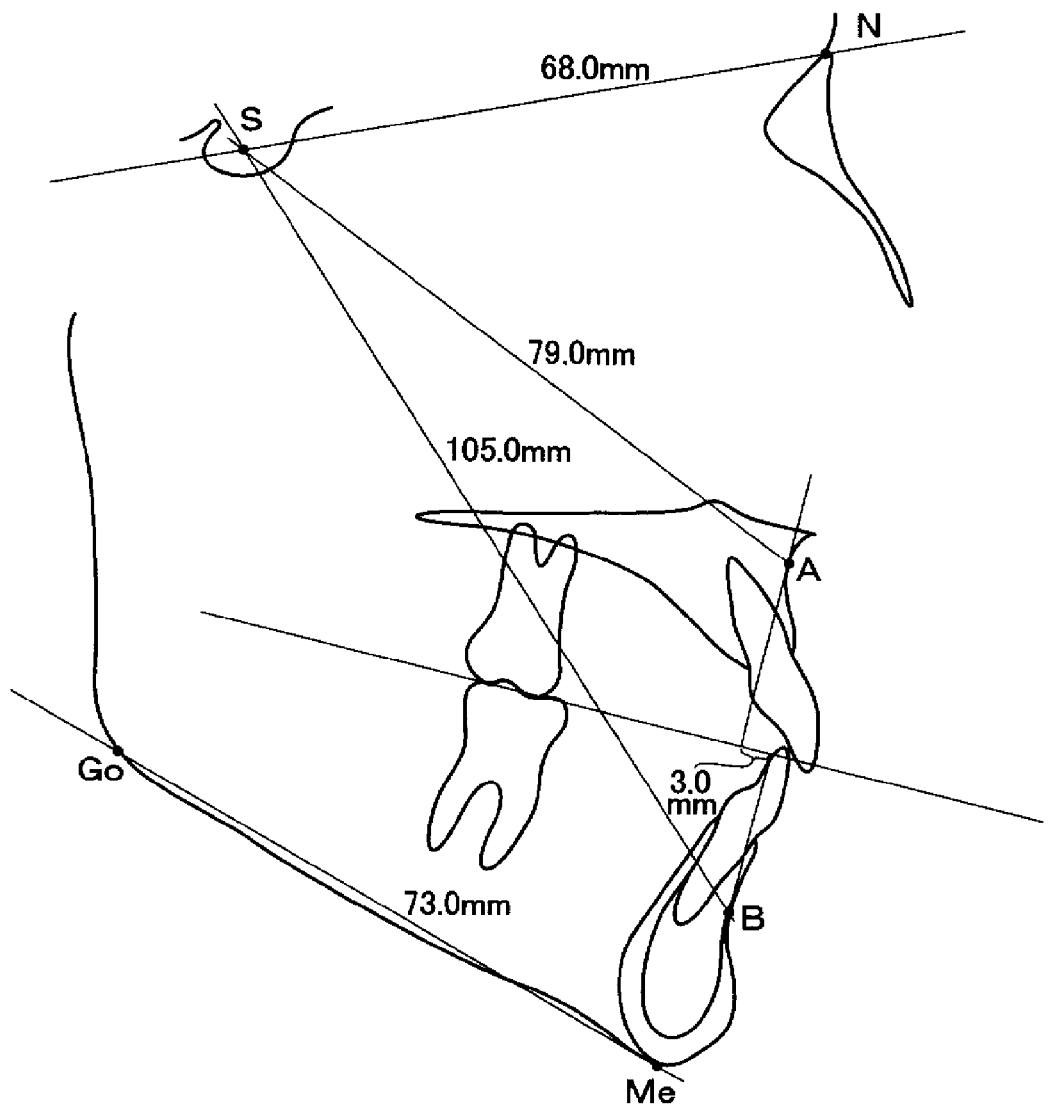
FIG. 14 is a tracing made based on a cephalometric radiogram of a patient 9.

From FIG. 14, the distances (S-A), (S-B) and (Go-Me) were measured. The results are: (S-A)=79.0 mm, (S-B)=105.0 mm and (Go-Me)=73.0 mm. Using the data, the calculation of P is given as follows: (105.0+73.0)/79.0=2.253. Therefore, the OPE index Q is 253. In this case, (S-N)=68.0 mm and Wits=3.0 mm.

As the OPE index Q is 253, it can be decided that patient 9 does not need to have the jaw operated on at the time of performing orthodontic treatment.

EXAMPLE 10

A cephalometric radiogram of patient 10 was taken. A tracing made based on the cephalometric radiogram is shown in FIG. 15.

Figure 15:
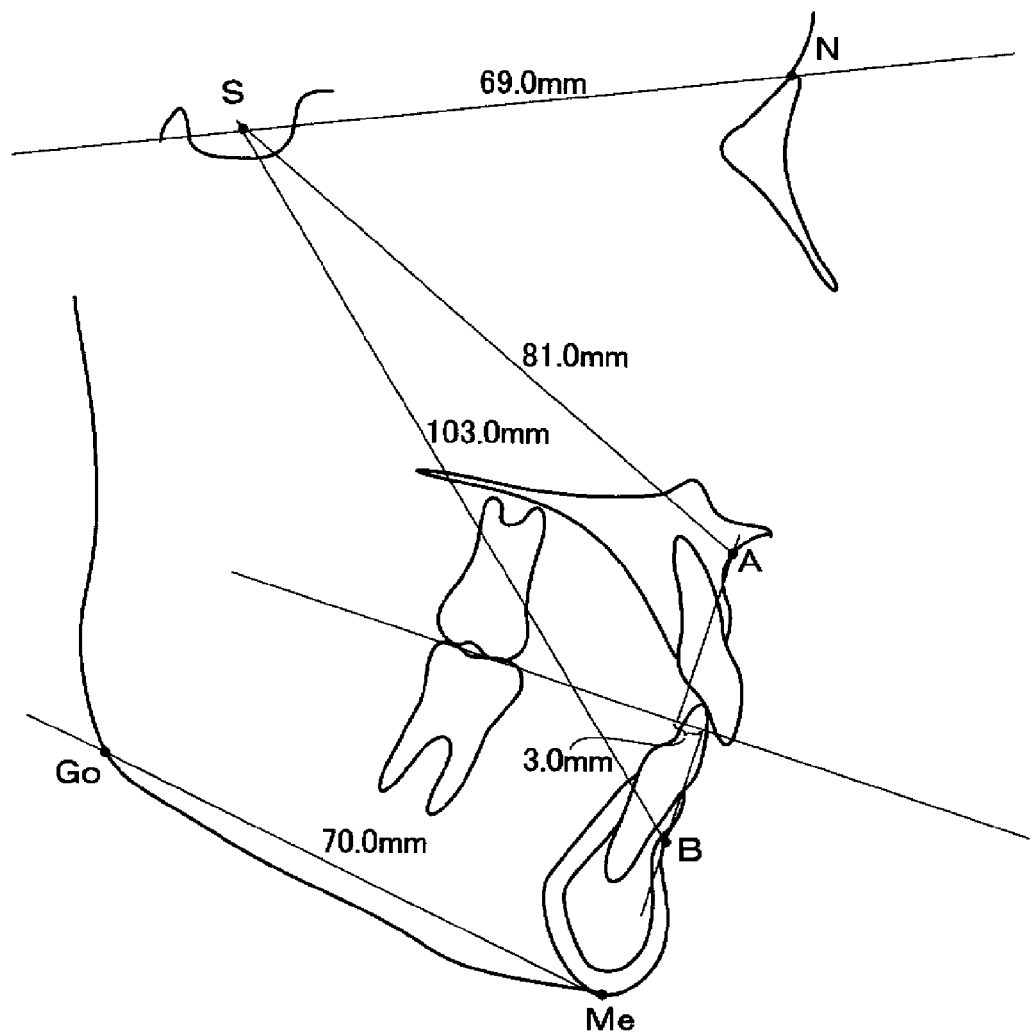
FIG. 15 is a tracing made based on a cephalometric radiogram of a patient 10.

From FIG. 15, the distances (S-A), (S-B) and (Go-Me) were measured. The results are: (S-A)=81.0 mm, (S-B)=103.0 mm and (Go-Me)=70.0 mm. Using the data, the calculation of P is given as follows: (103.0+70.0)/81.0=2.135. Therefore, the OPE index Q is 135. In this case, (S-N)=69.0 mm and Wits=3.0 mm.

It is a non-skeletal case, but the OPE index Q is 135, it can be decided that patient 10 does not need to have the jaw operated on at the time of performing orthodontic treatment, and orthodontic treatment by a non-tooth extraction treatment is applied.

EXAMPLE 11

A cephalometric radiogram of patient 11 was taken. A tracing made based on the cephalometric radiogram is shown in FIG. 16.

Figure 16:
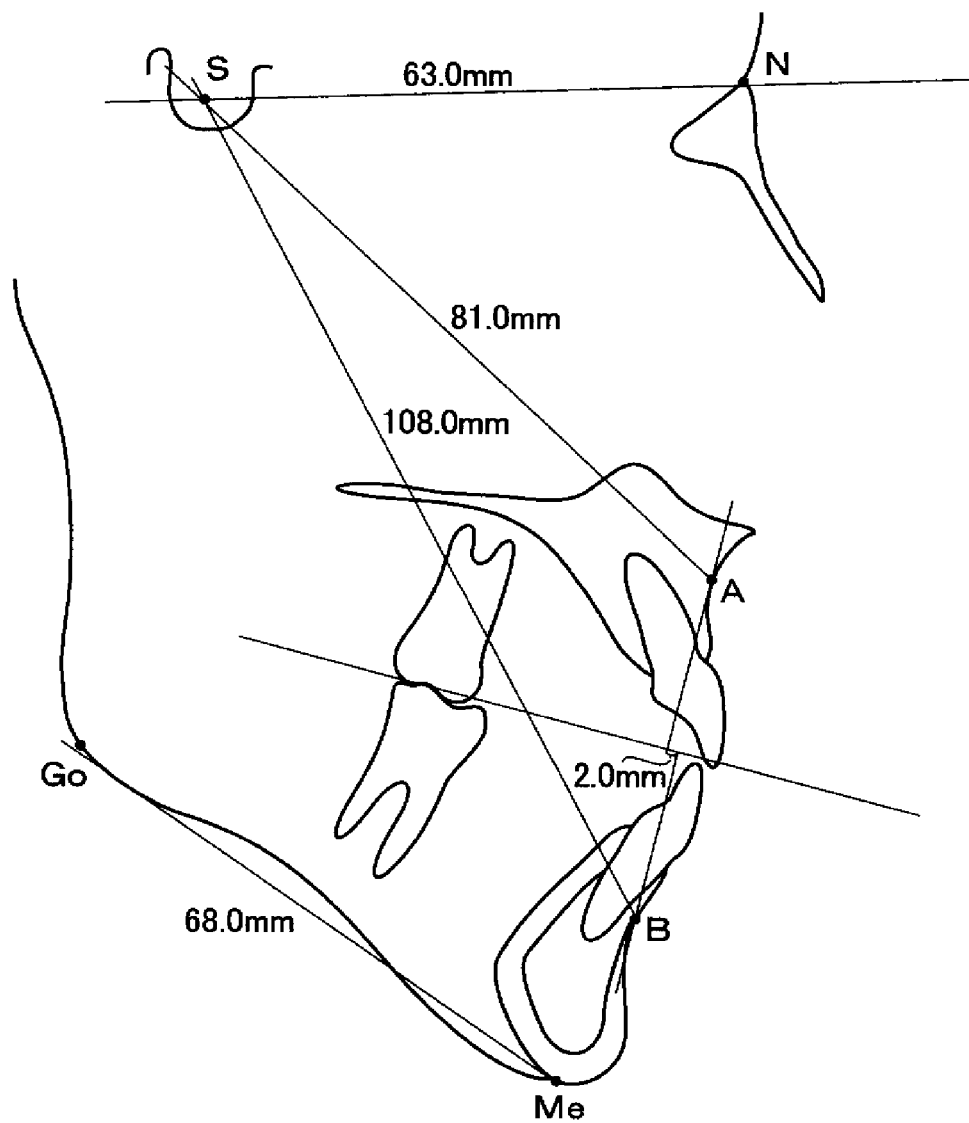
FIG. 16 is a tracing made based on a cephalometric radiogram of a patient 11.

From FIG. 16, the distances (S-A), (S-B) and (Go-Me) were measured. The results are: (S-A)=81.0 mm, (S-B)=108.0 mm and (Go-Me)=68.0 mm. Using the data, the calculation of P is given as follows: (108.0+68.0)/81.0=2.172. Therefore, the OPE index Q is 172. In this case, (S-N)=63.0 mm and Wits=2.0 mm.

The OPE index Q is 172 and Wits is 2.0 mm, which is a non-skeletal case, but it can be decided that patient 11 does not need the jaw to be operated on at the time of performing orthodontic treatment, and orthodontic treatment by a non-tooth extraction is applied.

EXAMPLE 12

A cephalometric radiogram of patient 12 was taken. A tracing made based on the cephalometric radiogram is shown in FIG. 17.

Figure 17:
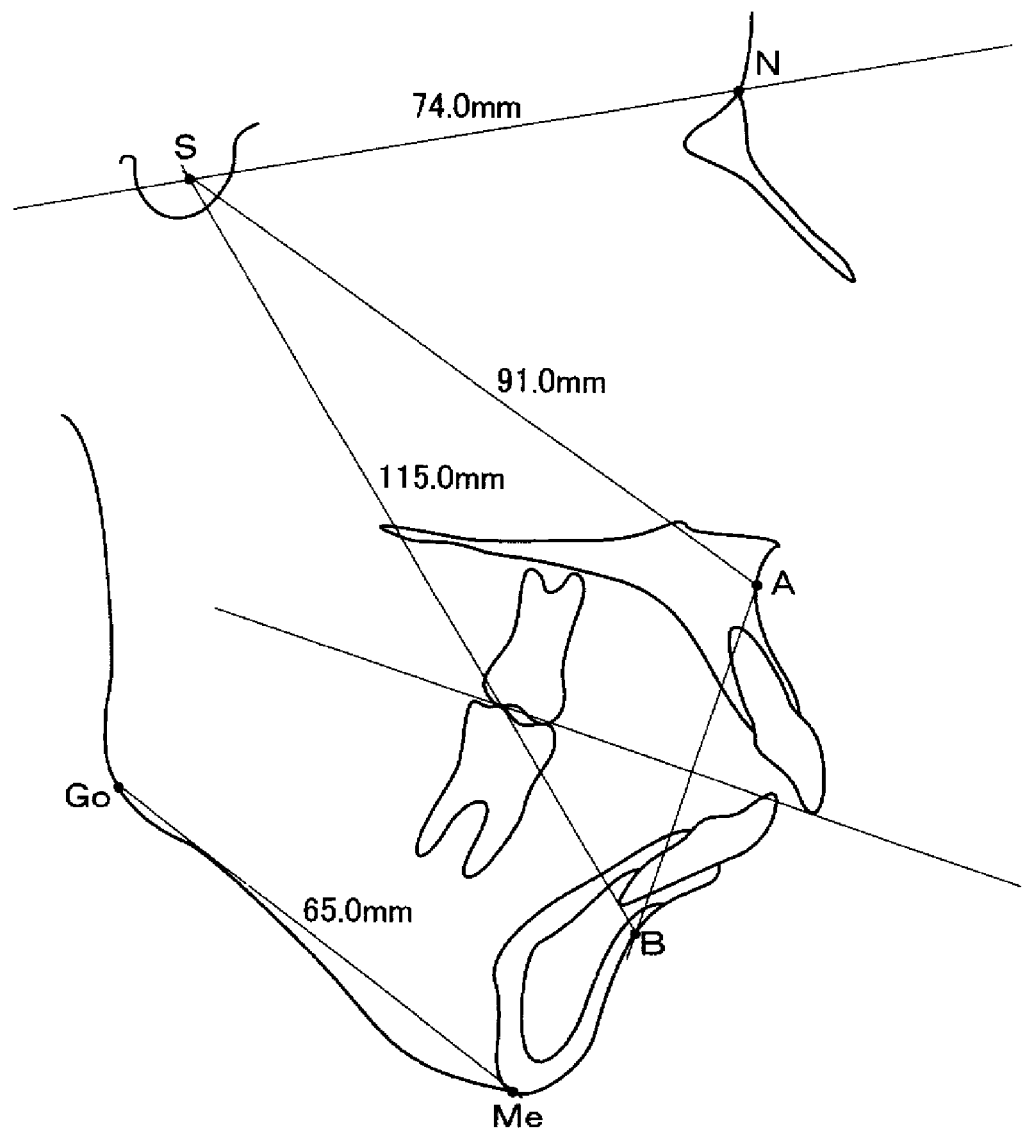
FIG. 17 is a tracing made based on a cephalometric radiogram of a patient 12.

From FIG. 17, the distances (S-A), (S-B) and (Go-Me) were measured. The results are: (S-A)=91.0 mm, (S-B)=115.0 mm and (Go-Me)=65.0 mm. Using the data, the calculation of P is given as follows: (115.0+65.0)/91.0=1.978. Therefore, the OPE index Q is -22. In this case, (S-N)=74.0 mm and Wits=0 mm.

As the OPE index Q is -22, it a borderline case. Generally, in case of $-50 \leq Q < 0$, at the time of performing orthodontic treatment, the necessity of operating on the jaw becomes high, but this is a case of mandible with a strong retrograde growth tendency, it can be decided that the patient 12 does not need to have the jaw operated on at the time of performing orthodontic treatment.

Figure 18:
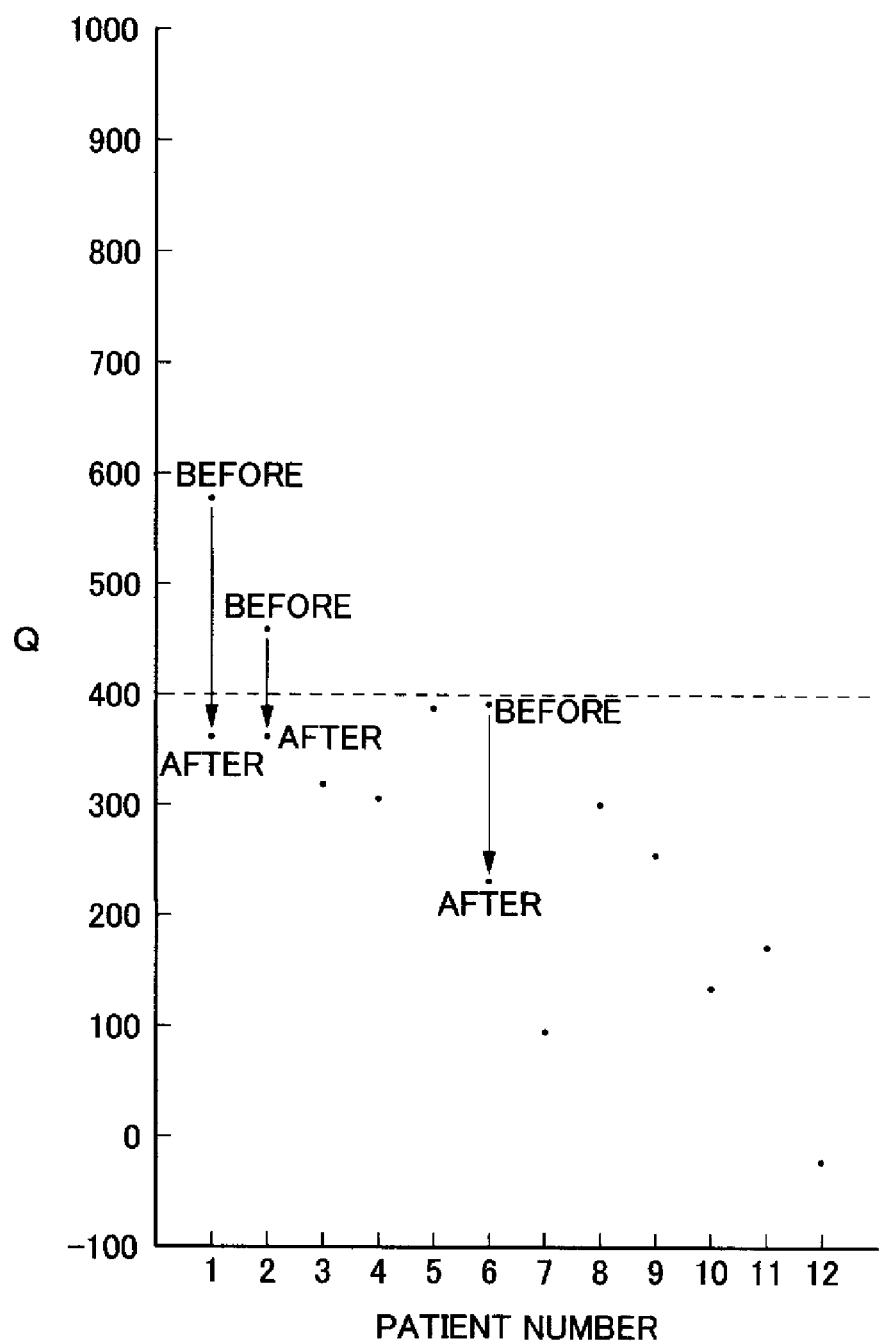
FIG. 18 is a schematic diagram showing results of calculation of OPE index Q of the patients 1 to 12.

The results of calculation of OPE index Q of patients 1 to 12 are summarized in FIG. 18.

As explained, according to the method of calculating an index for deciding the necessity of surgically operating on the jaw according to the first embodiment, the OPE index Q can be calculated by using the distances (S-A), (S-B) and (Go-Me) which are measured by cephalometric radiography. And, based on the OPE index Q, without being influenced by the experience of a dentist, the necessity of the surgical operation on the jaw in orthodontic treatment can be decided correctly within a short period of time, moreover with a certain objectivity.

Next explained is the second embodiment.

In the second embodiment, a method of deciding the necessity of surgically operating on the jaw in orthodontic treatment is explained.

Figure 19:
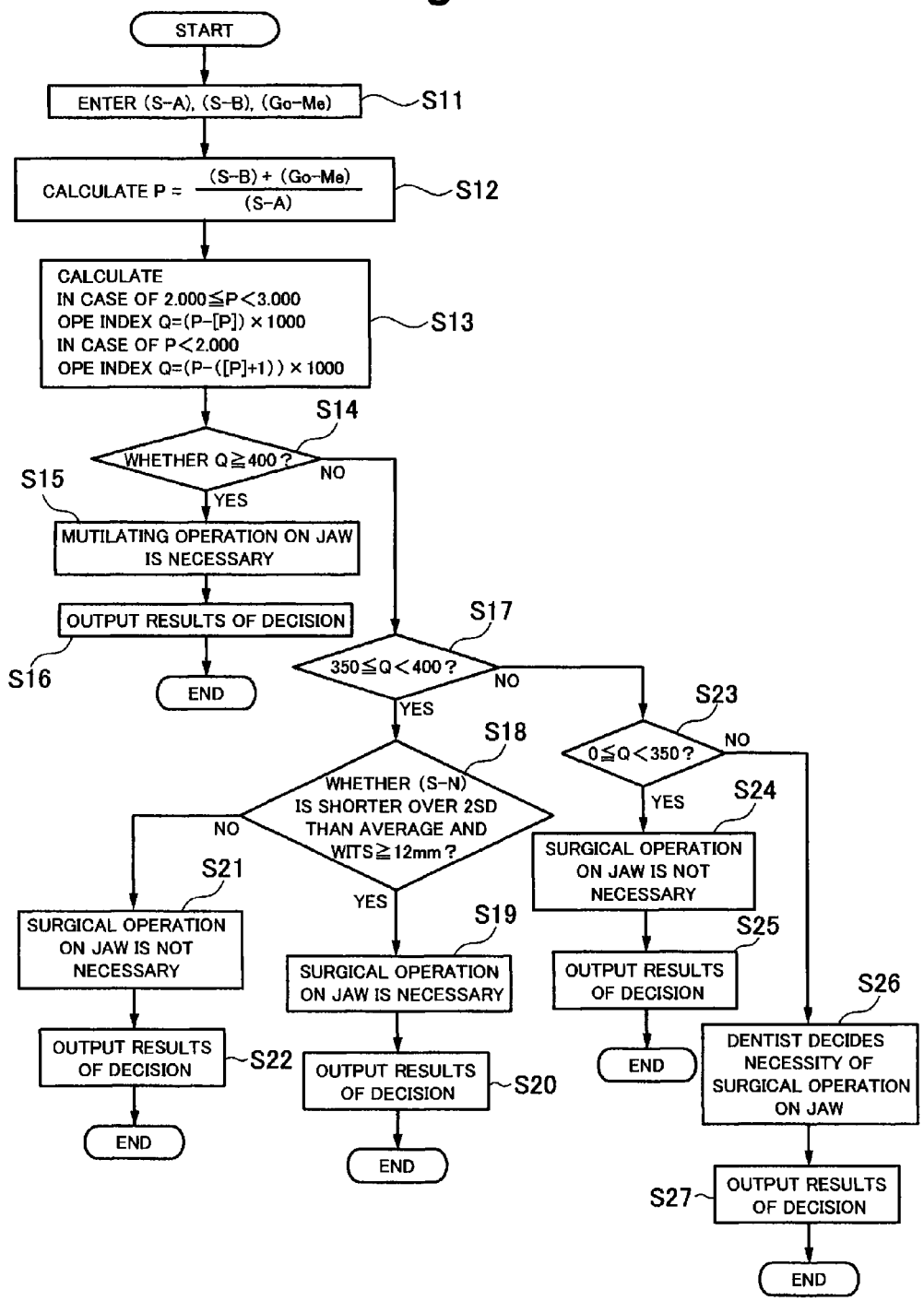
FIG. 19 is a flowchart showing a method of deciding the necessity of surgically operating on the jaw in orthodontic treatment according to the second embodiment of the present invention.

A flowchart of the method of deciding the necessity of surgically operating on the jaw is shown in FIG. 19. According to the flowchart, a program is created, and is executed on a computer.

As the same as the first embodiment, before executing the method of deciding the necessity of surgically operating on the jaw, the distances (S-A), (S-B) and (Go-Me) are measured.

As shown in FIG. 19, in step S11, the distances (S-A), (S-B) and (Go-Me) which are measured as the above are entered.

In step S12, from the entered (S-A), (S-B) and (Go-Me), P is calculated according to $$P=((S\text{-}B)+(Go\text{-}Me))/(S\text{-}A).$$

In step S13, from P obtained by the calculation of the above, whether $2.000 \leq P < 3.000$ or $P < 2.000$ is decided. As the result of the decision, in case of $2.000 \leq P < 3.000$, omitting the figures of the fourth decimal place and under of P, the OPE index Q is calculated according to $$Q=(P-[P]) \times 1000),$$

and in case of P<2.000, the OPE index Q is calculated according to $$Q=(P-([P]+1)) \times 1000.$$

In step S14, the OPE index Q calculated in this way is decided whether equal to or larger than 400, or not.

In step S15, in case that the OPE index Q is equal to or larger than 400, in orthodontic treatment, it is decided that the severing operation on the mandible is necessary.

In step S16, the result of the decision that the severing operation on the jaw is necessary is output on a display, for example.

In step S14, in the case that Q is decided not to be equal to nor larger than 400, in step S17, Q is decided whether equal to or larger than 350, or less than 400, or not.

In case that the OPE index Q is equal to or larger than 350, and less than 400, in step S18, it is decided whether the distance (S-N) is shorter than over 2SD than the average, and Wits is equal to or larger than 12 mm or not. If applicable, in step S19, it is decided whether the surgical operation on the jaw is necessary.

When being decided that the surgical operation on the jaw is necessary, in step S20, the result of the decision is output on a display, for example.

In step S18, when being decided whether the distance (S-N) is not shorter than over 2SD than the average, and Wits is not equal to nor larger than 12 mm, in step S21, it is decided that the surgical operation on the jaw is not necessary.

When being decided that the surgical operation on the jaw is not necessary, in step S22, the result of the decision is output on a display, for example.

In step S17, in case that Q is decided not to be equal to or larger than 350, and not equal to nor less than 400, in step S23, it is decided whether Q is equal to or larger than 0 and less than 350, or not.

When being decided whether the OPE index Q is equal to or larger than 0 and less than 350, in step S24, it is decided whether the surgical operation on the jaw is not necessary.

When being decided that the surgical operation on the jaw is not necessary, in step S25, the results of the decision is output on a display, for example.

In case that the OPE index Q is not decided to be equal to or larger than 0 and less than 350, the OPE index Q becomes negative. In this case, in step S26, a dentist decides the necessity of the surgical operation on the jaw, in step S27, the result of diagnosis is output on a display, for example.

According to the method of deciding the necessity of surgically operating on the jaw, according to the second embodiment, (based on the OPE index Q to be calculated using the distances (S-A), (S-B) and (Go-Me) which are measured by cephalometric radiography, in orthodontic treatment) the necessity of the surgical operation on the jaw can be decided correctly within a short period of time, moreover with a certain objectivity, without being influenced by the experience of a dentist.

Next explained is the third embodiment.

In the third embodiment, a method of calculating an OPE index as an index for deciding the necessity of surgically operating on the jaw in orthodontic treatment is explained.

Figure 20:
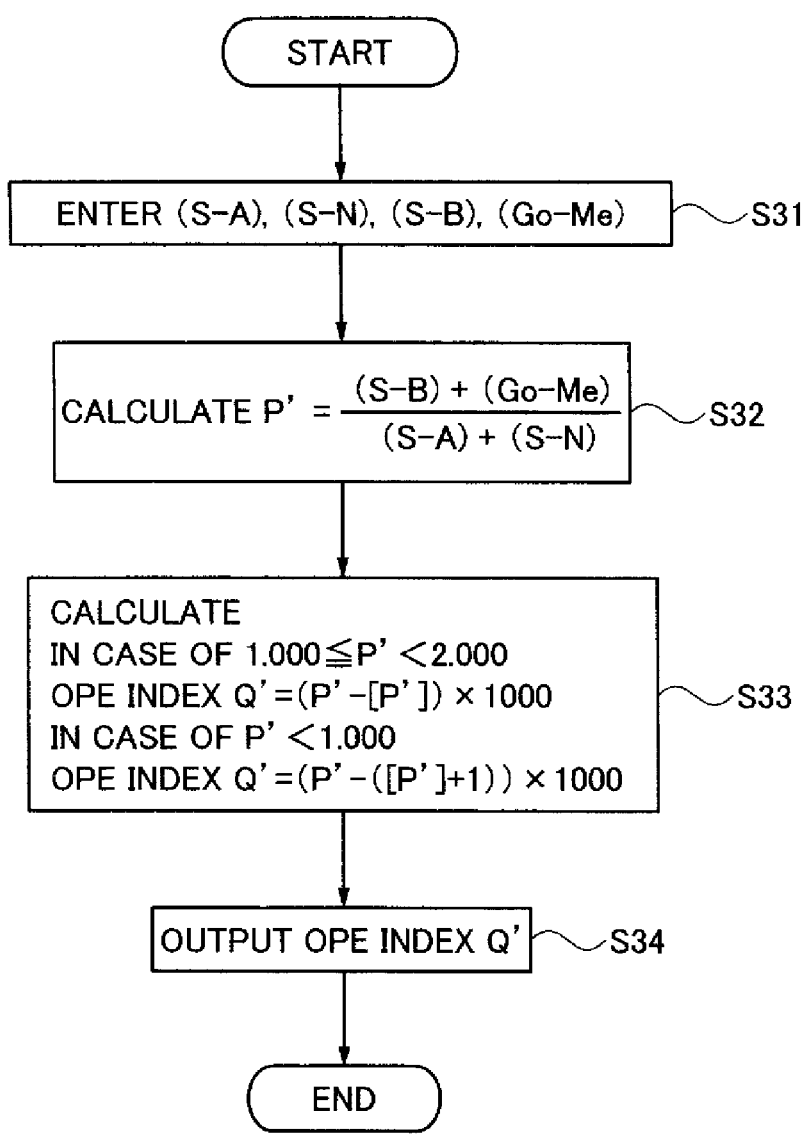
FIG. 20 is a flowchart showing a method of calculating an index for deciding the necessity of surgically operating on the jaw in orthodontic treatment according to the third embodiment of the present invention.

A flowchart of the method of the calculation is shown in FIG. 20. According to the flowchart, a program is created, and is executed on a computer.

Before making the calculation, taking a cephalometric radiogram of a patient to be treated by orthodontic treatment, the distances (S-A), (S-N), (S-B) and (Go-Me) are measured. The measurement of the distances can be made by entering the coordinate data of measured points of S, A, N, B, Go and Me on the cephalometric radiogram by using a pen tablet or a digitizer, for example. Or, the image data obtained by cephalometric radiography is taken in a computer, and the coordinates of S, A, N, B, Go and Me are measured from the image data, and from the coordinates which are measured like this, the distances (S-A), (S-N), (S-B) and (Go-Me) may be obtained by calculations.

As shown in FIG. 20, in step S31, the distances (S-A), (S-N), (S-B) and (Go-Me) which are measured by the above are entered.

In step S32, from the entered (S-A), (S-N), (S-B) and (Go-Me), P' is calculated according to $P'=((S-B)+(Go-Me))/((S-A)+(S-N))$.

In step S33, omitting the figures of the fourth decimal place and under of P' obtained by the calculation, in case of $1.000 \leq P' < 2.000$, the OPE index Q' is calculated according to $Q'=(P'-[P'])\times 1000$, and in case of P'<1.000, the OPE index Q' is calculated according to $Q'=(P'-([P']+1))\times 1000$.

In step S34, the OPE index Q' calculated as the above is output on a display, for example.

In case that the OPE index Q' calculated as the above is equal to or larger than 330, in orthodontic treatment, it can be diagnosed that the severing operation on the jaw, typically the mandible, is necessary. Also, in the case that the OPE index Q' is equal to or larger than 270 and less than 330, which is a borderline case, by Wits analysis, a supplementary analysis is added. In the case that the result of Wits analysis is equal to or larger than 12 mm, it is decided that the surgical application, in other words, the surgical operation on the jaw, is necessary.

In the case that the OPE index Q' is less than 330 and equal to or larger than 0, in orthodontic treatment, it can be diagnosed that the surgical operation on the jaw is not necessary.

In case that the OPE index Q' is negative, also, denoting that a strong retrograde growth tendency of the mandible or an overgrowth tendency of the maxilla, it is necessary to consider the surgical operation on the jaw.

Generally, in addition to the OPE index Q', a dentist finally decides the necessity of operating the jaw combining other inspection results such as the conventional cephalometric analysis focusing mainly on angle measurement, etc.

EXAMPLE 13

By FIG. 3 showing the tracing made based on the cephalometric radiogram of patient 1 taken in the example 1, the distances (S-A), (S-N), (S-B) and (Go-Me) were measured. The results are: (S-A)=78.0 mm, (S-N)=67.0 mm, (S-B)=123.0 mm and (Go-Me)=78.0 mm. Using the data, the calculation of P' is given as follows: (123.0+78.0)/(78.0+67.0)=1.386. Therefore, the OPE index Q' is 386. In this case, Wits=17.0 mm.

As the OPE index Q' is 386, it can be decided that patient 1 needs the severing operation on the mandible in orthodontic treatment.

Therefore, the necessary severing operation on the mandible was performed. By FIG. 4 showing the tracing made based on the cephalometric radiogram after the severing operation on the mandible of patient 1 taken in the example 1, the distances (S-A), (S-N), (S-B) and (Go-Me) were measured. The results are: (S-A)=78.0 mm, (S-N)=67.0 mm, (S-B)=111.0 mm and (Go-Me)=73.0 mm. Using the data, the calculation of P' is given as follows: (111.0+73.0)/(78.0+67.0)=1.268. Therefore, the OPE index Q' is 268. In this case, Wits=4.0 mm.

As the OPE index Q' is 268, it can be decided that patient 1 is able to be treated by orthodontic treatment with the results of the severing operation on the mandible.

EXAMPLE 14

By FIG. 5 showing the tracing made based on the cephalometric radiogram of patient 2 taken in the example 2, the distances (S-A), (S-N), (S-B) and (Go-Me) were measured. The results are: (S-A)=83.0 mm, (S-N)=69.0 mm, (S-B)=123.0 mm and (Go-Me)=81.0 mm. Using the data, the calculation of P' is given as follows: (123.0+81.0)/(83.0+69.0)=1.342. Therefore, the OPE index Q' is 342. In this case, Wits=16.0 mm.

As the OPE index Q' is 342, it can be decided that patient 2 needs the severing operation on the mandible.

Therefore, the necessary severing operation on the mandible was performed. By FIG. 6 showing the tracing made based on the cephalometric radiogram taken after the severing operation on the mandible of the patient 2, the distances (S-A), (S-N), (S-B) and (Go-Me) were measured. The results are: (S-A)=83.0 mm, (S-N)=69.0 mm, (S-B)=116.0 mm and (Go-Me)=80.0 mm. Using the data, the calculation of P' is given as follows: (116.0+80.0)/(83.0+69.0)=1.289. Therefore, the OPE index Q' is 289. In this case, Wits=6.0 mm.

As the OPE index Q' is 289, it can be decided that patient 2 is able to be treated orthodontic treatment with the results of the severing operation on the mandible.

EXAMPLE 15

By FIG. 7 showing the tracing made based on the cephalometric radiogram of patient 3 taken in the example 3, the distances (S-A), (S-N), (S-B) and (Go-Me) were measured. The results: (S-A)=88.0 mm, (S-N)=67.0 mm, (S-B)=126.0 mm and (Go-Me)=78.0 mm. Using the data, the calculation of P' is given as follows: (126.0+78.0)/(88.0+67.0)=1.316. Therefore, the OPE index Q' is 316. In this case, Wits=7.0 mm.

This is a case of light skeletal class III, but as the OPE index Q' is 316, it can be decided that the patient 3 does not need to have the jaw operated on at the time of performing orthodontic treatment.

EXAMPLE 16

By FIG. 8 showing the tracing made based on the cephalometric radiogram of the patient 4 taken in the example 4, the distances (S-A), (S-N), (S-B) and (Go-Me) were measured. The results: (S-A)=85.0 mm, (S-N)=64.0 mm, (S-B)=119.0 mm and (Go-Me)=77.0 mm. Using the data, the calculation of P' is given as follows: (119.0+77.0)/(85.0+64.0)=1.315. Therefore, the OPE index Q' is 315. In this case, Wits=9.0 mm.

This a case of skeletal class III, but as the OPE index Q' is 315, it can be decided that patient 4 does not need to have the jaw operated on at the time of performing orthodontic treatment.

EXAMPLE 17

By FIG. 9 showing the tracing made based on the cephalometric radiogram of the patient 5 taken in the example 5, the distances (S-A), (S-N), (S-B) and (Go-Me) were measured. The results: (S-A)=75.0 mm, (S-N)=65.0 mm, (S-B)=109.0 mm and (Go-Me)=70.0 mm. Using the data, the calculation of P' is given as follows: (109.0+70.0)/(75.0+65.0)=1.278. Therefore, the OPE index Q' is 278. In this case, Wits=10.0 mm.

As the OPE index Q' is 278, it a borderline case. Wits is 10.0 mm, which a very strong skeletal case, however, the Wits was equal to or less than 12 mm, further with (S-N)=65.0 mm, so it can be decided that the jaw operation is not necessary at the time of performing orthodontic treatment.

EXAMPLE 18

By FIG. 10 showing the tracing made based on the cephalometric radiogram of patient 6 taken in the example 6, the distances (S-A), (S-N), (S-B) and (Go-Me) were measured. The results: (S-A)=87.0 mm, (S-N)=68.0 mm, (S-B)=128.0 mm and (Go-Me)=80.0 mm. Using the data, the calculation of P' is given as follows: (128.0+80.0)/(87.0+68.0)=1.341. Therefore, the OPE index Q' is 341. In this case, Wits=12.0 mm.

As the OPE index Q' is 341, it a borderline case. Wits 12.0 mm, further with (S-N)=68.0 mm which a skeletal class III, and it can be decided as a dentofacial deformity, and decided that the severing operation on the mandible necessary.

Therefore, the necessary severing operation on the mandible was performed. By FIG. 11 showing the tracing made based on the cephalometric radiogram taken after the severing operation on the mandible of patient 6, the distances (S-A), (S-N), (S-B) and (Go-Me) were measured. The results are: (S-A)=87.0 mm, (S-N)=68.0 mm, (S-B)=121.0 mm and (Go-Me)=73.0 mm. Using the data, the calculation of P' is given as follows: (121.0+73.0)/(87.0+68.0)=1.251. Therefore, the OPE index Q' is 251. In this case, Wits=5.0 mm.

As the OPE index Q' is 251, it can be decided that patient 6 is able to be treated by orthodontic treatment with the results of the severing operation on the mandible.

EXAMPLE 19

By FIG. 12 showing the tracing made based on the cephalometric radiogram of patient 7 taken in the example 7, the distances (S-A), (S-N), (S-B) and (Go-Me) were measured. The results: (S-A)=86.0 mm, (S-N)=67.0 mm, (S-B)=111.0 mm and (Go-Me)=69.0 mm. Using the data, the calculation of P' is given as follows: (111.0+69.0)/(86.0+67.0)=1.176. Therefore, the OPE index Q' is 176. In this case, Wits=0 mm.

The OPE index Q' is 176, and there a retrograde growth tendency of the mandible, but it can be decided that the patient 7 does not need to have the jaw operated on at the time of performing orthodontic treatment, and orthodontic treatment by a tooth extracting is applied.

EXAMPLE 20

By FIG. 13 showing the tracing made based on the cephalometric radiogram of patient 8 taken in the example 8, the distances (S-A), (S-N), (S-B) and (Go-Me) were measured. The results: (S-A)=90.0 mm, (S-N)=68.0 mm, (S-B)=127.0 mm and (Go-Me)=80.0 mm. Using the data, the calculation of P' is given as follows: (127.0+80.0)/(90.0+68.0)=1.310. Therefore, the OPE index Q' is 310. In this case, Wits=11.0 mm.

As the OPE index Q' is 310, it can be decided that patient 8 does not need to have the jaw operated on at the time of performing orthodontic treatment.

EXAMPLE 21

By FIG. 14 showing the tracing made based on the cephalometric radiogram of patient 9 taken in the example 9, the distances (S-A), (S-N), (S-B) and (Go-Me) were measured. The results: (S-A)=79.0 mm, (S-N)=68.0 mm, (S-B)=105.0 mm and (Go-Me)=73.0 mm. Using the data, the calculation of P' is given as follows (105.0+73.0)/(79.0+68.0)=1.210. Therefore, the OPE index Q' is 210. In this case, Wits=3.0 mm.

As the OPE index Q' is 210, it can be decided that patient 9 does not need to have the jaw operated on at the time of performing orthodontic treatment.

EXAMPLE 22

By FIG. 15 showing the tracing made based on the cephalometric radiogram of patient 10 taken in the example 10, the distances (S-A), (S-N), (S-B) and (Go-Me) were measured. The results: (S-A)=81.0 mm, (S-N)=69.0 mm, (S-B)=103.0 mm and (Go-Me)=70.0 mm. Using the data, the calculation of P' is given as follows: (103.0+70.0)/(81.0+69.0)=1.153. Therefore, the OPE index Q' is 153. In this case, Wits=4.0 mm.

This is a case of non-skeletal, but the OPE index Q' is 153, therefore, it can be decided that the patient 10 does not need to have the jaw operated on at the time of performing orthodontic treatment, and orthodontic treatment by a non-tooth extraction treatment is applied.

EXAMPLE 23

By FIG. 16 showing the tracing made based on the cephalometric radiogram of patient 11 taken in the example 11, the distances (S-A), (S-N), (S-B) and (Go-Me) were measured. The results: (S-A)=81.0 mm, (S-N)=63.0 mm, (S-B)=108.0 mm and (Go-Me)=68.0 mm. Using the data, the calculation of P' is given as follows: (108.0+68.0)/(81.0+63.0)=1.222. Therefore, the OPE index Q' is 222. In this case, Wits=2.0 mm.

As the OPE index Q' is 222, and Wits is 2.0 mm, which is a non-skeletal case, but it can be decided that patient 11 does not need to have the jaw operated on at the time of performing orthodontic treatment, and orthodontic treatment by a non-tooth extraction treatment is applied.

EXAMPLE 24

By FIG. 17 showing the tracing made based on the cephalometric radiogram of patient 12 taken in the example 12, the distances (S-A), (S-N), (S-B) and (Go-Me) were measured. The results: (S-A)=91.0 mm, (S-N)=74.0 mm, (S-B)=115.0 mm and (Go-Me)=65.0 mm. Using the data, the calculation of P' is given as follows: (115.0+65.0)/(91.0+74.0)=1.090. Therefore, the OPE index Q' is 90. In this case, Wits=0.0 mm.

As the OPE index Q' is 90, it a borderline case. The patient 12 has a strong retrograde growth tendency of the mandible, and it can be decided that patient 12 does not need to have the jaw operated on at the time of performing orthodontic treatment.

As explained, by the method of calculating an index for deciding the necessity of surgically operating on the jaw according to the third embodiment, using the distances of (S-A), (S-N), (S-B) and (Go-Me) which are measured by cephalometric radiography, the OPE index Q' can be calculated. And, based on the OPE index Q', without being influenced by the experience of a dentist, the necessity of the surgical operation on the jaw in orthodontic treatment can be diagnosed correctly within a short period of time, moreover with a certain objectivity.

Next explained is the fourth embodiment.

In the fourth embodiment, the method of deciding the necessity of surgically operating on the jaw in orthodontic treatment is explained.

Figure 21:
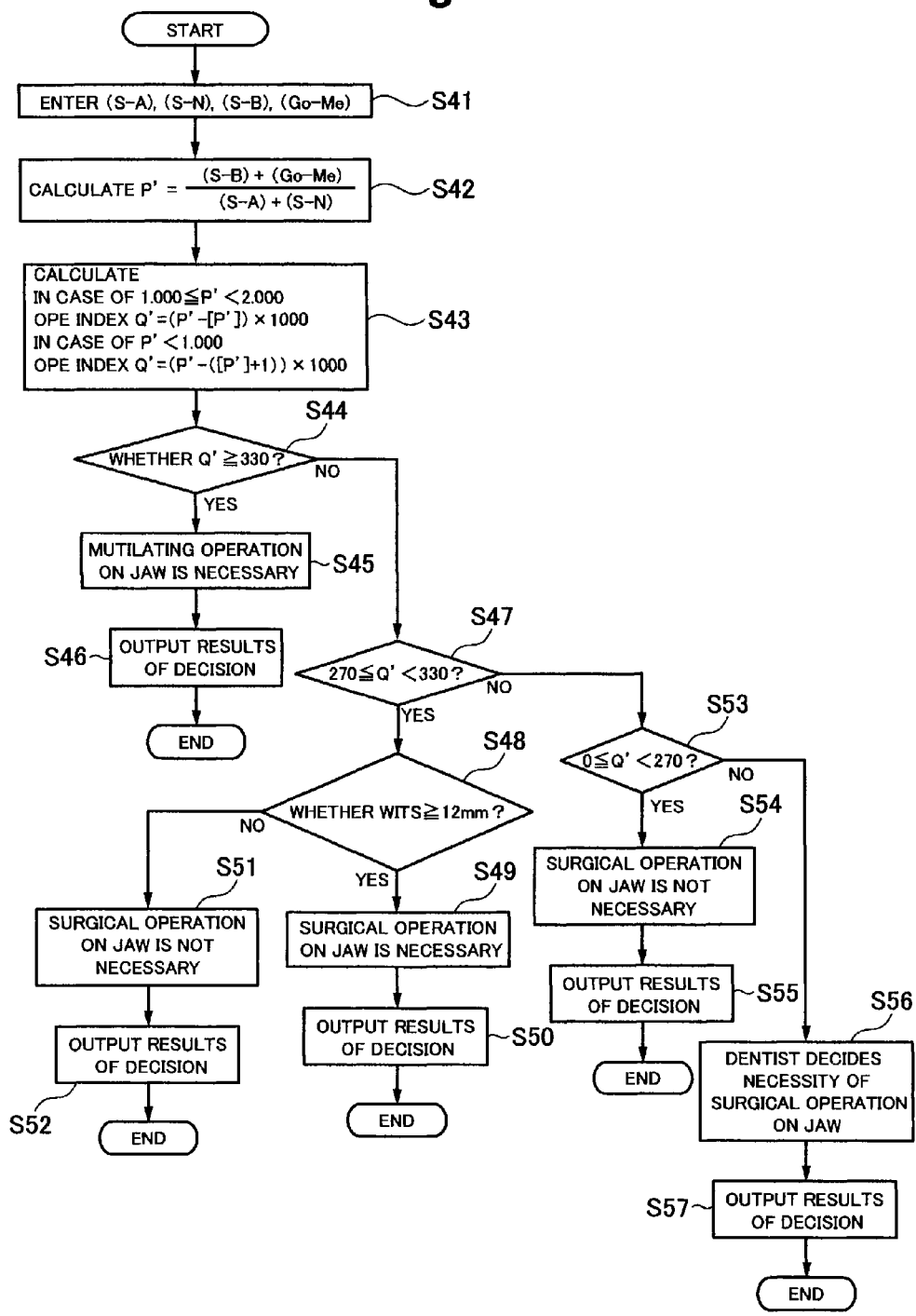
FIG. 21 is a flowchart showing a method of deciding the necessity of surgically operating on the jaw in orthodontic treatment according to the fourth embodiment of the present invention.

A flowchart of the method of deciding the necessity of surgically operating on the jaw is shown in FIG. 21. A program is created according to the flowchart, and is executed on a computer.

As the same as the third embodiment, before executing the method of deciding the necessity of surgically operating on the jaw, the distances (S-A), (S-N), (S-B) and (Go-Me) are measured.

As shown in FIG. 21, in step S41, the distances (S-A), (S-N), (S-B) and (Go-Me) which are measured by the above are entered.

In step S42, from the entered (S-A), (S-N), (S-B) and (Go-Me), P' is calculated according to $$P'=((S-B)+(Go-Me))/((S-A)+(S-N)).$$

In step S43, from P' obtained by the calculation, it is decided whether $1.000 \leq P' < 2.000$ or $P' < 1.000$. As the result of decision, in the case of $1.000 \leq P' < 2.000$, omitting the figures of the fourth decimal place and under of P', the OPE index Q' is calculated according to, $$Q'=(P'-[P'])\times 1000,$$

and in case of P'<1.000, the OPE index Q' is calculated according to $$Q'=(P'-([P']+1))\times 1000.$$

In step S44, the OPE index Q' calculated as the above is decided whether equal to or larger than 330 or not.

In step S45, in the case that the OPE index Q' is equal to or larger than 330, in orthodontic treatment, it is decided that the severing operation on the jaw, typically the mandible is necessary.

In step S46, the result of the decision, that the severing operation on the jaw is necessary, is output on a display, for example.

In step S44, in the case that Q' is decided not to be equal to nor larger than 330, in step S47, Q' is decided whether equal to or larger than 270 and less than 330, or not.

In step S48, in the case that the OPE index Q' is equal to or larger than 270, and less than 330, Wits is decided whether equal to or larger than 12 mm, or not. If Wits is equal to or larger than 12 mm, in step S49, it is decided that the surgical operation on the jaw is necessary.

When being decided that the surgical operation on the jaw is necessary, in step S50, the result of the decision is output on a display, for example.

In step S48, when Wits is decided not to be equal to nor larger than 12 mm, in step S51, it is decided that the surgical operation on the jaw is not necessary.

When being decided that the surgical operation on the jaw is not necessary, in step S52, the result of the decision is output on a display, for example.

In step S47, in the case that Q' is decided not to be equal to nor larger than 270, and not equal to nor less than 330, in step S53, Q' is decided whether equal to or larger than 0 and less than 270 or not.

When the OPE index Q' is decided to be equal to or larger than 0 and less than 270, in step S54, it is decided that the surgical operation on the jaw is not necessary.

When being decided that the surgical operation on the jaw is not necessary, in step S55, the result of the decision is output on a display, for example.

In case that the OPE index Q' is not decided to be equal to or larger than 0 and less than 270, the OPE index Q' becomes negative. In this case, in step S56, a dentist decides the necessity of the surgical operation on the jaw, in step S57, the result of the decision is output on a display, for example.

By the method of deciding the necessity of surgically operating on the jaw according to the fourth embodiment, based on the OPE index Q' to be calculated by using the distances (S-A), (S-N), (S-B) and (Go-Me) which are measured by cephalometric radiography, without being influenced by the experience of a dentist, the necessity of the surgical operation on the jaw in orthodontic treatment can be decided correctly with a short period of time, moreover with a certain objectivity.

Next explained is the fifth embodiment.

In the fifth embodiment, an index for deciding disharmony of the maxilla and mandible can be calculated as the same as the method of calculating the index for deciding the necessity of surgically operating on the jaw in orthodontic treatment explained in the first embodiment.

According to the fifth embodiment, the index for deciding disharmony of the maxilla and mandible can be calculated. And based on the index for deciding disharmony of the maxilla and mandible, without being influenced by the experience of a dentist, disharmony of the maxilla and mandible in dental treatment such as orthodontic treatment, etc. can be decided correctly with a short period of time, moreover with a certain objectivity.

Next explained is the sixth embodiment.

In the sixth embodiment, the method of deciding disharmony of the maxilla and mandible is executed as the same as the method of deciding the necessity of surgically operating on the jaw in orthodontic treatment as explained in the second embodiment.

According to the sixth embodiment, based on the index for deciding disharmony of the maxilla and mandible, without being influenced by the experience of a dentist, disharmony of the maxilla and mandible in dental treatment such as orthodontic treatment, etc. can be decided correctly within a short period of time, moreover with a certain objectivity.

Next explained is the seventh embodiment.

In the seventh embodiment, an index for deciding disharmony of the maxilla and mandible is calculated as the same as the method of calculating the index for deciding the necessity of surgically operating on the jaw in orthodontic treatment explained in the third embodiment.

According to the seventh embodiment, the same advantages as the fifth embodiment can be obtained.

Next explained is the eighth embodiment.

In the eighth embodiment, the method of deciding disharmony of the maxilla and mandible is executed as the same as the method of deciding the necessity of surgically operating on the jaw in orthodontic treatment as explained in the fourth embodiment.

According to the eighth embodiment, the same advantages as the sixth embodiment can be obtained.

Next explained is the ninth embodiment.

In the ninth embodiment, an index for deciding dentofacial deformity can be calculated as the same as the method of calculating the index for deciding the necessity of surgically operating on the jaw in orthodontic treatment explained in the first embodiment.

According to the ninth embodiment, the index for deciding dentofacial deformity can be calculated. And based on the index for deciding dentofacial deformity, without being influenced by the experience of a doctor or a dentist, dentofacial deformity can be decided correctly within a short period of time, moreover with a certain objectivity.

Next explained is the tenth embodiment.

In the tenth embodiment, the method of deciding dentofacial deformity is executed as the same as the method of deciding the necessity of surgically operating on the jaw in orthodontic treatment explained in the second embodiment.

According to the tenth embodiment, based on the index for deciding dentofacial deformity, without being influenced by the experience of a doctor or a dentist, dentofacial deformity can be decided correctly within a short period of time, moreover with a certain objectivity.

Next explained is the eleventh embodiment.

In the eleventh embodiment, an index for deciding dentofacial deformity is calculated as the same as the method of calculating the index for deciding the necessity of surgically operating on the jaw in orthodontic treatment explained in the third embodiment.

According to the eleventh embodiment, the same advantages as the ninth embodiment can be obtained.

Next explained is the twelfth embodiment.

In the twelfth embodiment, the method of deciding dentofacial deformity is executed as the same as the method of deciding the necessity of surgically operating on the jaw in orthodontic treatment explained in the fourth embodiment.

According to the twelfth embodiment, the same advantages as the tenth embodiment can be obtained.

Here, a data processor which is used in the execution of the method of calculating an index for deciding the necessity of surgically operating on the jaw, the method of deciding the necessity of surgically operating on the jaw, the method of calculating an index for deciding disharmony of the maxilla and mandible, the method of deciding disharmony of the maxilla and mandible, the method of calculating an index for deciding dentofacial deformity, or the method of deciding dentofacial deformity based on the first to the twelfth embodiments is explained.

Figure 22:
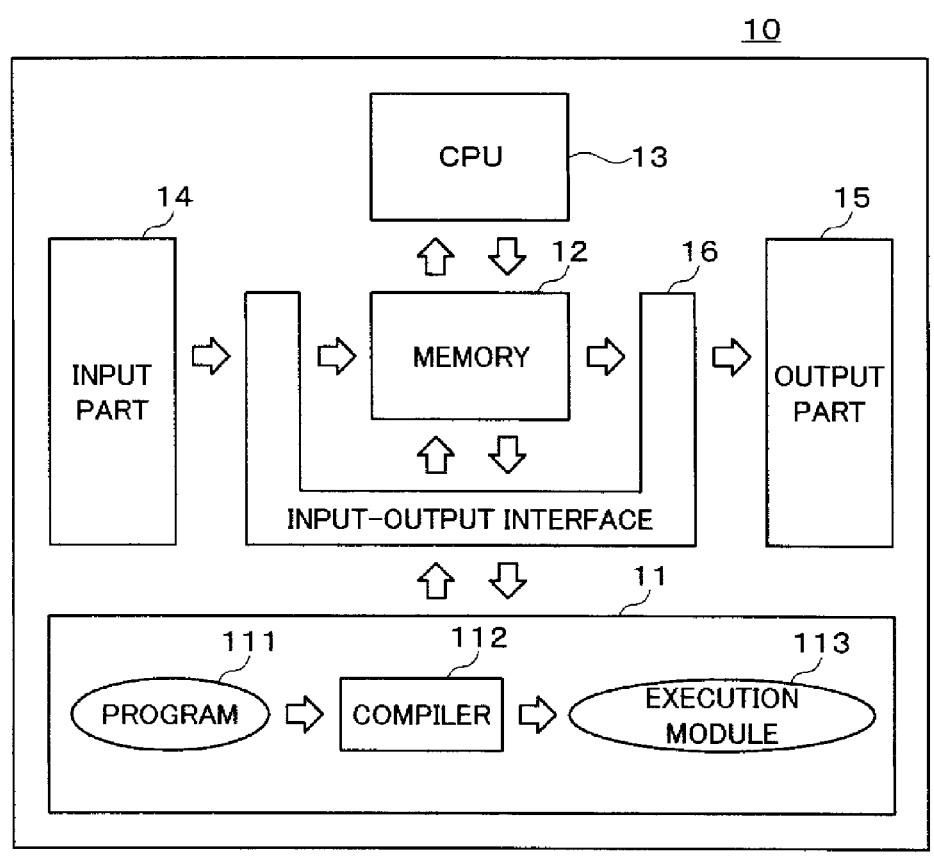
FIG. 22 is a schematic drawing showing a data processor to be used for execution of the method of calculating an index for deciding the necessity of surgically operating on the jaw, the method of deciding the necessity of surgically operating on the jaw, the method of calculating an index for deciding disharmony of the maxilla and mandible, the method of deciding disharmony of the maxilla and mandible, the method of calculating an index for deciding dentofacial deformity, or the method of deciding dentofacial deformity according to the first to the twelfth embodiments of the present invention.

FIG. 22 shows an example of the data processor 10. As shown in FIG. 22, the data processor 10 is comprised of an auxiliary storage device 11, a memory 12, a CPU (Central Processing Unit) 13 as a processing part, an input part 14, an output part 15 and an input-output interface 16.

The auxiliary storage device 11 is a device to store various kinds of information. For example, the auxiliary storage device 11 is comprised of a hard disk, a ROM (Read Only Memory), etc. The auxiliary storage device 11 stores a program 111, a compiler 112 and an execution module 113.

The program 111 is, for example, a program (source program) describing the processing on the flowcharts shown in FIG. 2, FIG. 19, FIG. 20 or FIG. 21. The compiler 112 compiles and links the program 111. The execution module 113 is a module which is compiled and linked by the compiler 112.

The memory 12 is a temporary storing means to store various kinds of information, and is comprised of a RAM (Random Access Memory), etc., for example. The CPU 13 executes various types of arithmetic processing such as addition, subtraction, multiplication and division, etc., and plays a role executing the execution module 13 through the memory 12 and the input-output interface 16. The input part 14 is an input device to enter various kinds of execution commands, etc. The output part 15 is an output device to output the various kinds of execution results, etc. The input-output interface 16 mediates the input-output between each composition element of the data processor 10.

Next, the operation of the data processor 10 comprised as described above is explained. First, the compiled commands entered from the input part 14 by an operator, are stored in the memory 12 through the input-output interface 16. In the memory 12, the program 111 of the auxiliary storage device 11 is compiled and linked by the compiler 112, and the execution module 113, which is a machine language code, is generated.

Next, by entering the execution commands from the input part 14 by an operator, the CPU 13 loads the execution module 113 in the memory 12. When the execution module 113 is loaded in the memory 12, by the CPU 13, each processing on the flowcharts shown in FIG. 2, FIG. 19, FIG. 20 or FIG. 21 is sequentially called to the CPU 13 from the memory 12, after executing each processing, the execution results are stored in the memory 12. The execution results stored in the memory 12, by the CPU 13, are output to the output part 15 through the input-output interface 16.

For example, in the case of calculating the OPE index executing the processing on the flowchart shown in FIG. 2, the following steps are taken. First, the execution module 113 to realize step S1 for input processing is called to the CPU 13 from the memory 12. In step S1, the data (distances (S-A), (S-B) and (Go-Me)) entered from the input part 14 by an operator are loaded to the memory 12. Finishing the input processing of step S1 to realize step S2 of a calculation processing, the execution module 113 is called to the CPU 13 from the memory 12. In step S2, P is calculated by the entered data. Finishing the calculation processing of step 2, to realize step S3 the execution module 113 is called to the CPU 13 from the memory 12. In step S3, according to the size of P, the OPE index is calculated. Finishing the calculation processing of step S3, to realize step S4 the execution module 113 is called to the CPU 13 from the memory 12. In step S4, the value of P is output to the output part 15 as the calculation results.

In the case of performing the processing on the flowcharts shown in FIG. 19, FIG. 20 or FIG. 21, the processing is the same as the above.

It should be understood that various changes and modifications to the embodiments described herein will be apparent to those skilled in the art. Such changes and modifications can be made without departing from the spirit and scope of the present subject matter and without diminishing its intended advantages. It is therefore intended that such changes and modifications be covered by the appended claims.

For example, numerical numbers, flowcharts, etc. presented in the aforementioned embodiments and examples are only examples, and the different numerical numbers, flowcharts, etc. may be used as necessary.

The invention claimed is:

1. A method of calculating an index related to at least one of orthodontic treatment, dental treatment, and dentofacial deformity, the method comprising:
   receiving user input through an input device, by a processing device, of points of measurement from a cephalometric radiogram, the points of measurement comprising:
      "S" representing Sella, a central point of the pot-shaped shaded image of the sella turcica of the sphenoid bone;
      "A" representing the deepest point on the median sagittal plane between the forefront of the anterior nasal spine, which is on the forefront part of the palatine shelf of maxilla and the Prosthion, which is the most frontal point of an alveolar process between the upper central incisors;
      "B" representing the deepest point between the infradentale, the most front point of the alveolar process between the lower central incisors and pogonion, the most prominent point of the mandibular mental protuberance for the Frankfort plane;
      "Go" representing Gonion, a cross point of the angle of the mandible and the bisector of the cross angle between the line connecting the posterior plane of the head of the temporomandibular joint and the posterior part of the angle of the mandible and the mandibular plane; and
      "Me" representing the menton, the lowest point of the median section image of a chin;
   measuring, by a processing device, distances comprising:
      (S-A) representing the distance between points S and A;
      (S-B) representing the distance between points S and B; and
      (Go-Me) representing the distance between points Go and Me; and
   calculating, by a processing device, P=((S-B)+(Go-Me))/(S-A),
   wherein the index is for at least one of deciding the necessity of surgically operating on the jaw in orthodontic treatment, deciding disharmony of the maxilla and mandible in dental treatment, and deciding dentofacial deformity.

2. The method of calculating an index according to claim 1, further comprising omitting the figures of the fourth decimal place and under of P and calculating, by a processing device:

$Q=(P-[P])\times1000$ ([] denotes Gauss's symbol) (where $2.000 \leq P < 3.000$)

or $Q=(P-([P]+1))\times1000$ ([] denotes Gauss's symbol) (where $P<2.000$).

3. A method of deciding at least one of the necessity of surgically operating on the jaw in orthodontic treatment, disharmony of the maxilla and mandible in dental treatment, and dentofacial deformity, the method comprising:
   receiving user input through an input device, by a processing device, of points of measurement from a cephalometric radiogram, the points of measurement comprising:
      "S" representing Sella, a central point of the pot-shaped shaded image of the sella turcica of the sphenoid bone;
      "A" representing the deepest point on the median sagittal plane between the forefront of the anterior nasal spine, which is on the forefront part of the palatine shelf of maxilla and the Prosthion, which is the most frontal point of an alveolar process between the upper central incisors;
      "B" representing the deepest point between the infradentale, the most front point of the alveolar process between the lower central incisors and pogonion, the most prominent point of the mandibular mental protuberance for the Frankfort plane;
      "Go" representing Gonion, a cross point of the angle of the mandible and the bisector of the cross angle between the line connecting the posterior plane of the head of the temporomandibular joint and the posterior part of the angle of the mandible and the mandibular plane; and
      "Me" representing the menton, the lowest point of the median section image of a chin;
   measuring, by a processing device, distances comprising:
      (S-A) representing the distance between points S and A;
      (S-B) representing the distance between points S and B; and
      (Go-Me) representing the distance between points Go and Me; and
   calculating, by a processing device, P=((S-B)+(Go-Me))/(S-A) and with such value of P or further omitting the figures of the fourth decimal place and under of P and calculating, by a processing device:

$Q=(P-[P])\times1000$ ([] denotes Gauss's symbol) (where $2.000 \leq P < 3.000$)

or $Q=(P-([P]+1))\times1000$ ([] denotes Gauss's symbol) (where $P<2.000$); and deciding at least one of the necessity of surgically operating on the jaw, deciding disharmony of the maxilla and mandible, and whether a patient suffers from dentofacial deformity by determining whether calculated P or Q is equal to or larger than a predetermined value or not, respectively.

4. The method according to claim 3, wherein P≥2.400 or Q≥400 is determined for deciding at least one of the necessity of surgically operating on the jaw in orthodontic treatment and dentofacial deformity.

5. The method according to claim 3 wherein Wits analysis is performed and it is determined whether Wits≥12 mm or not for deciding dentofacial deformity.

6. A system for calculating an index related to at least one of orthodontic treatment, dental treatment, and dentofacial deformity, based on points of measurement identified from a cephalometric radiograph, the points of measurement comprising:
"S" representing Sella, a central point of the pot-shaped shaded image of the sella turcica of the sphenoid bone;
"A" representing the deepest point on the median sagittal plane between the forefront of the anterior nasal spine, which is on the forefront part of the palatine shelf of maxilla and the Prosthion, which is the most frontal point of an alveolar process between the upper central incisors;
"B" representing the deepest point between the infradentale, the most front point of the alveolar process between the lower central incisors and pogonion, the most prominent point of the mandibular mental protuberance for the Frankfort plane;
"Go" representing Gonion, a cross point of the angle of the mandible and the bisector of the cross angle between the line connecting the posterior plane of the head of the temporomandibular joint and the posterior part of the angle of the mandible and the mandibular plane; and
"Me" representing the menton, the lowest point of the median section image of a chin,
the system comprising:
a processor;
a module, operating on the processor, for calculating the index related to at least one of orthodontic treatment, dental treatment, and dentofacial deformity, the module comprising:
a module for receiving user input through an input device of the points of measurement;
a module for measuring distances comprising:
(S-A) representing the distance between points S and A;
(S-B) representing the distance between points S and B; and
(Go-Me) representing the distance between points Go and Me; and
a module for calculating P=((S-B)+(Go-Me))/(S-A).

7. The system of claim 6, further comprising a module for omitting the figures of the fourth decimal place and under of P and calculating:

$$Q=(P-[P])\times 1000 \text{ ([] denotes Gauss's symbol) (where } 2.000 \leq P < 3.000)$$

or $$Q=(P-([P]+1))\times 1000 \text{ ([] denotes Gauss's symbol)} \text{ (where } P<2.000).$$

8. A system for deciding at least one of the necessity of surgically operating on the jaw in orthodontic treatment, disharmony of the maxilla and mandible in dental treatment, and dentofacial deformity, based on points of measurement identified from a cephalometric radiograph, the points of measurement comprising:
"S" representing Sella, a central point of the pot-shaped shaded image of the sella turcica of the sphenoid bone;
"A" representing the deepest point on the median sagittal plane between the forefront of the anterior nasal spine, which is on the forefront part of the palatine shelf of maxilla and the Prosthion, which is the most frontal point of an alveolar process between the upper central incisors;
"B" representing the deepest point between the infradentale, the most front point of the alveolar process between the lower central incisors and pogonion, the most prominent point of the mandibular mental protuberance for the Frankfort plane;
"Go" representing Gonion, a cross point of the angle of the mandible and the bisector of the cross angle between the line connecting the posterior plane of the head of the temporomandibular joint and the posterior part of the angle of the mandible and the mandibular plane; and
"Me" representing the menton, the lowest point of the median section image of a chin;
a module, operating on the processor, for deciding at least one of the necessity of surgically operating on the jaw in orthodontic treatment, disharmony of the maxilla and mandible in dental treatment, and dentofacial deformity, the module comprising:
a module for receiving user input through an input device of the points of measurement;
a module for measuring distances comprising:
(S-A) representing the distance between points S and A;
(S-B) representing the distance between points S and B; and
(Go-Me) representing the distance between points Go and Me; and
a module for calculating P=((S-B)+(Go-Me))/(S-A) and with such value of P or further omitting the figures of the fourth decimal place and under of P, for calculating:

$$Q=(P-[P])\times 1000 \text{ ([] denotes Gauss's symbol) (where } 2.000 \leq P < 3.000)$$

or $$Q=(P-([P]+1))\times 1000 \text{ ([] denotes Gauss's symbol)} \text{ (where } P<2.000).$$

9. The system according to claim 8, further comprising a module for determining P≥2.400 or Q≥400 for deciding at least one of the necessity of surgically operating on the jaw in orthodontic treatment and dentofacial deformity.

10. The system according to claim 8 further comprising a module for performing Wits analysis and for determining whether Wits≥12 mm or not for deciding dentofacial deformity.

11. A computer program product for calculating an index related to at least one of orthodontic treatment, dental treatment, and dentofacial deformity, the computer program product comprising:
a computer readable storage medium having computer readable program code embodied therewith, the computer readable program code comprising:
computer readable program code configured to receive user input through an input device of points of measurement on a cephalometric radiograph, the points of measurement comprising:
"S" representing Sella, a central point of the pot-shaped shaded image of the sella turcica of the sphenoid bone;
"A" representing the deepest point on the median sagittal plane between the forefront of the anterior nasal spine, which is on the forefront part of the palatine shelf of maxilla and the Prosthion, which is the most frontal point of an alveolar process between the upper central incisors;

"B" representing the deepest point between the infradentale, the most front point of the alveolar process between the lower central incisors and pogonion, the most prominent point of the mandibular mental protuberance for the Frankfort plane;

"Go" representing Gonion, a cross point of the angle of the mandible and the bisector of the cross angle between the line connecting the posterior plane of the head of the temporomandibular joint and the posterior part of the angle of the mandible and the mandibular plane; and "Me" representing the menton, the lowest point of the median section image of a chin;

computer readable program code configured to measure distances between the points of measurement, the distances measured comprising:

(S-A) representing the distance between points S and A;

(S-B) representing the distance between points S and B; and (Go-Me) representing the distance between points Go and Me; and computer readable program code configured to calculate P=((S-B)+(Go-Me))/(S-A).

12. A computer program product for deciding at least one of the necessity of surgically operating on the jaw in orthodontic treatment, disharmony of the maxilla and mandible in dental treatment, and dentofacial deformity, the computer program product comprising:

a computer readable storage medium having computer readable program code embodied therewith, the computer readable program code comprising:

computer readable program code configured to receive user input through an input device of points of measurement on a cephalometric radiogram, the points of measurement comprising:

"S" representing Sella, a central point of the pot-shaped shaded image of the sella turcica of the sphenoid bone;

"A" representing the deepest point on the median sagittal plane between the forefront of the anterior nasal spine, which is on the forefront part of the palatine shelf of maxilla and the Prosthion, which is the most frontal point of an alveolar process between the upper central incisors;

"B" representing the deepest point between the infradentale, the most front point of the alveolar process between the lower central incisors and pogonion, the most prominent point of the mandibular mental protuberance for the Frankfort plane;

"Go" representing Gonion, a cross point of the angle of the mandible and the bisector of the cross angle between the line connecting the posterior plane of the head of the temporomandibular joint and the posterior part of the angle of the mandible and the mandibular plane; and "Me" representing the menton, the lowest point of the median section image of a chin;

computer readable program code configured to measure distances between the points of measurement, the distances measured comprising:

(S-A) representing the distance between points S and A;

(S-B) representing the distance between points S and B; and (Go-Me) representing the distance between points Go and Me;

computer readable program code configured to calculate P=((S-B)+(Go-Me))/(S-A), and with such value of P or further omitting the figures of the fourth decimal place and under of P, the computer readable program code configured to calculate:

$Q=(P-[P])\times 1000$ ([] denotes Gauss's symbol) (where $2.000 \leq P < 3.000$)

or $Q=(P-([P]+1))\times 1000$ ([] denotes Gauss's symbol) (where $P < 2.000$); and computer readable program code configured to determine whether calculated P or Q is equal to or larger than a predetermined value or not, respectively.

* * * * *